United States Patent [19]

Kriesel

[11] Patent Number: 5,468,226
[45] Date of Patent: Nov. 21, 1995

[54] FLUID DELIVERY APPARATUS HAVING A STORED ENERGY SOURCE

[75] Inventor: Marshall S. Kriesel, St. Paul, Minn.

[73] Assignee: Science Incorporated, Bloomington, Minn.

[21] Appl. No.: 192,035

[22] Filed: Feb. 3, 1994

Related U.S. Application Data

[60] Division of Ser. No. 69,937, May 28, 1993, Pat. No. 5,336,188, which is a continuation-in-part of Ser. No. 46,438, May 18, 1993, Pat. No. 5,411,480, which is a continuation-in-part of Ser. No. 870,021, Apr. 17, 1992, Pat. No. 5,222,560, which is a continuation of Ser. No. 870,269, Apr. 17, 1992, Pat. No. 5,205,820, which is a continuation-in-part of Ser. No. 642,208, Jan. 16, 1991, Pat. No. 5,169,389, which is a continuation-in-part of Ser. No. 367,304, Jun. 16, 1990, Pat. No. 5,019,047.

[51] Int. Cl.⁶ ................................................. A61H 37/00
[52] U.S. Cl. ..................... 604/132; 604/246; 604/890.1; 128/DIG. 12
[58] Field of Search ................... 604/82, 83, 85, 604/131, 132, 151, 153, 246, 257, 890.1; 128/DIG. 12

[56] References Cited

U.S. PATENT DOCUMENTS

| | | | |
|---|---|---|---|
| 4,898,582 | 2/1990 | Faste | 604/141 |
| 4,968,301 | 11/1990 | di Palma et al. | 604/132 |
| 5,152,753 | 10/1992 | Laguette et al. | 604/153 |
| 5,169,390 | 12/1992 | Althayde et al. | 604/141 |
| 5,257,987 | 11/1993 | Althayde et al. | 604/892.1 |
| 5,290,240 | 3/1994 | Horres, Jr. | 604/131 |
| 5,298,025 | 3/1994 | Hessel et al. | 604/93 |

Primary Examiner—Corrine M. Maglione
Attorney, Agent, or Firm—J. E. Brunton

[57] ABSTRACT

An apparatus for accurately infusing medicinal agents into an ambulatory patient at specific rates over extended periods of time. The apparatus is of a compact, low profile, laminate construction and includes either an elastic distendable membrane, or a thin barrier member which, in cooperation with a thin planar base defines a fluid chamber having a fluid outlet. The apparatus includes an internal stored energy source which functions to controllably expel the medicinal agents from the apparatus. The stored energy source may comprise either a distendable elastomeric membrane of an expandable sponge like cellular mass.

8 Claims, 15 Drawing Sheets

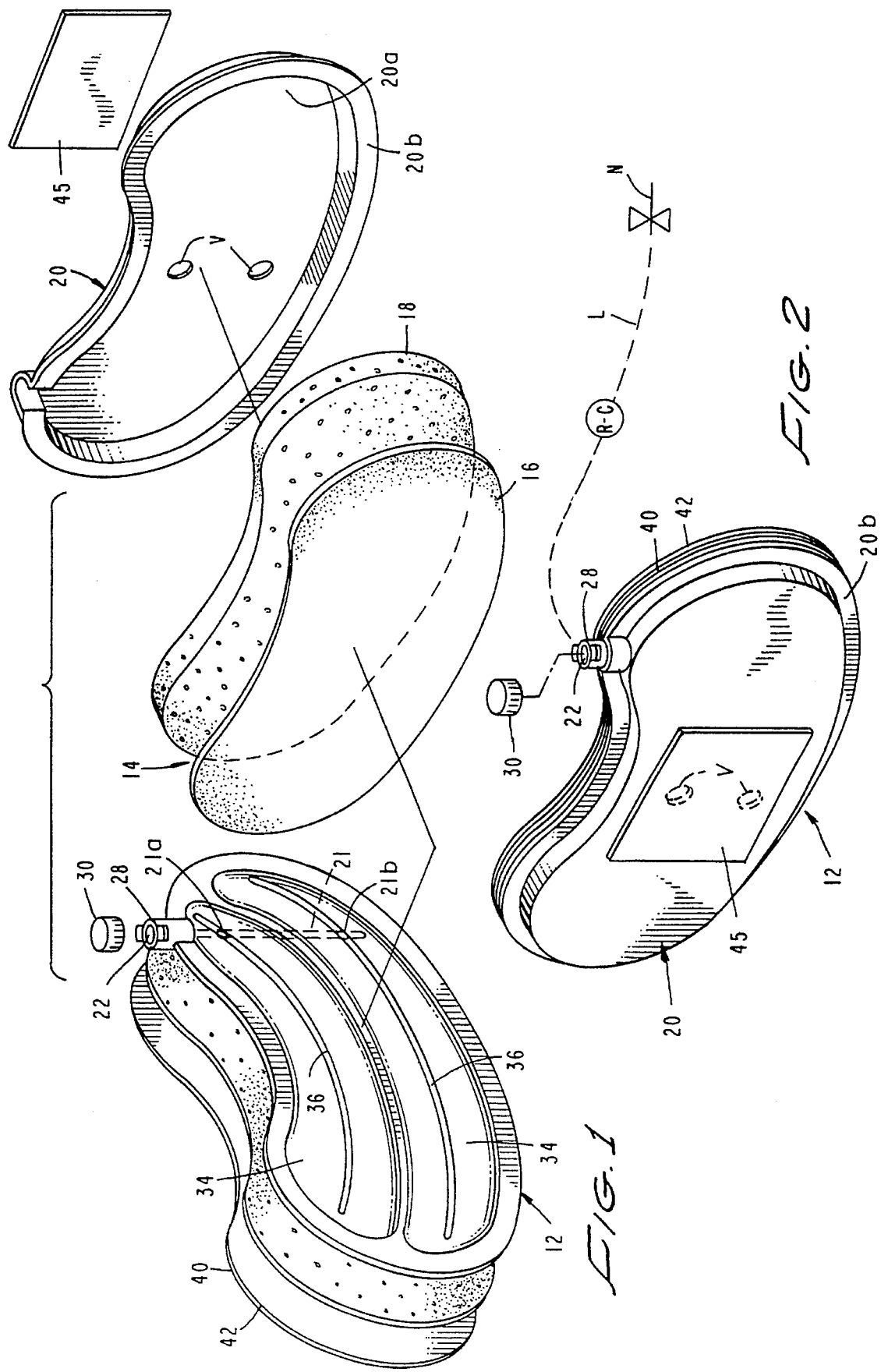

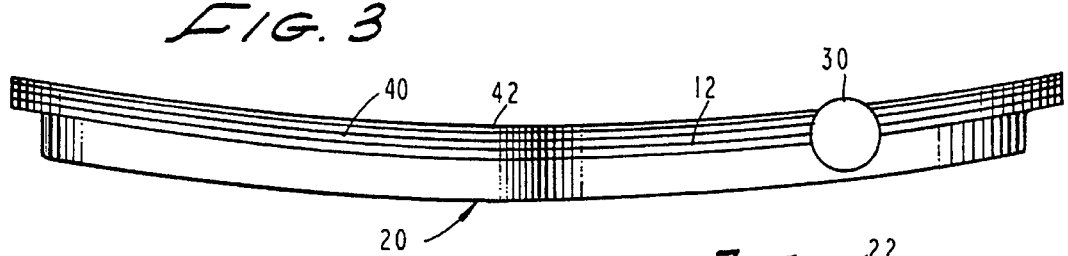
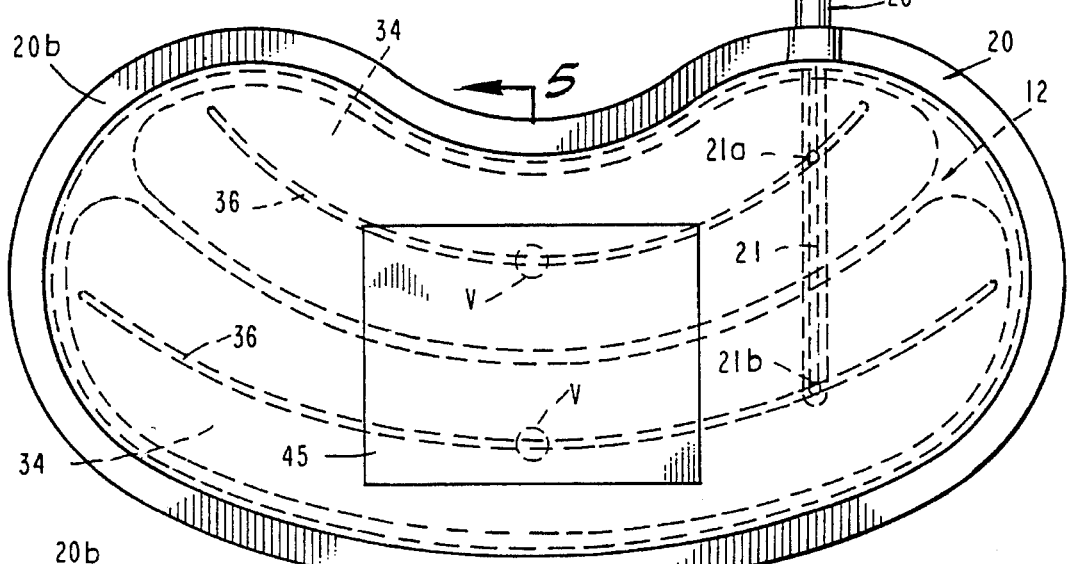
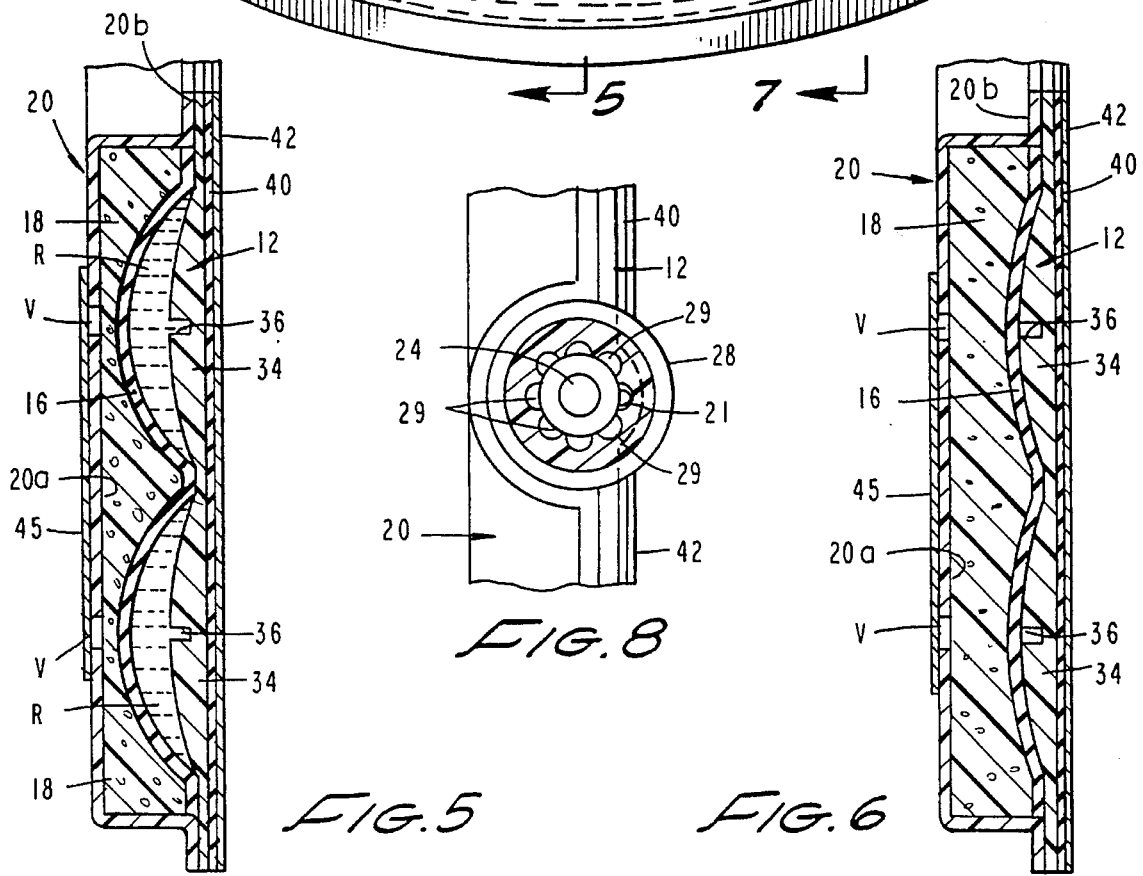

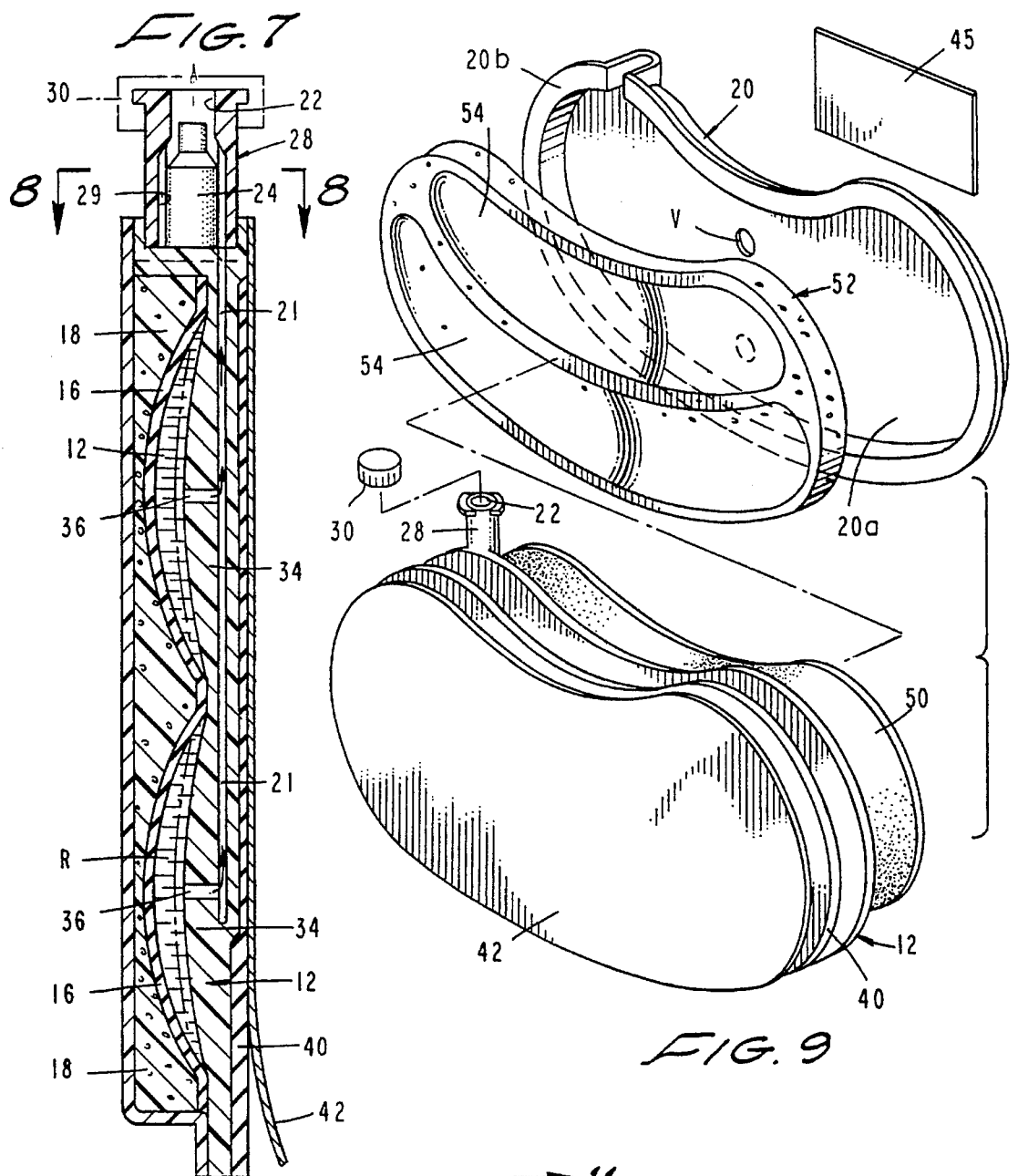

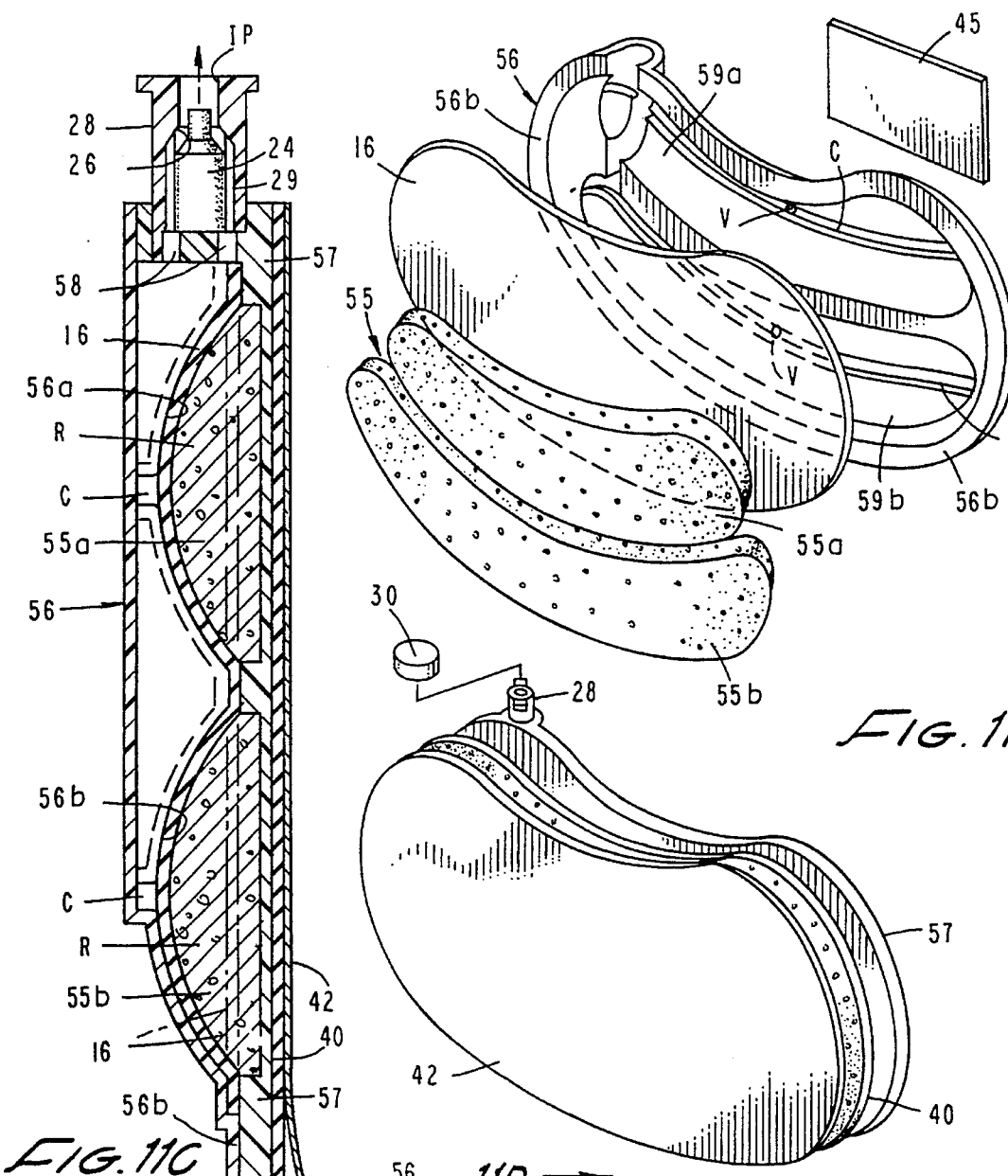
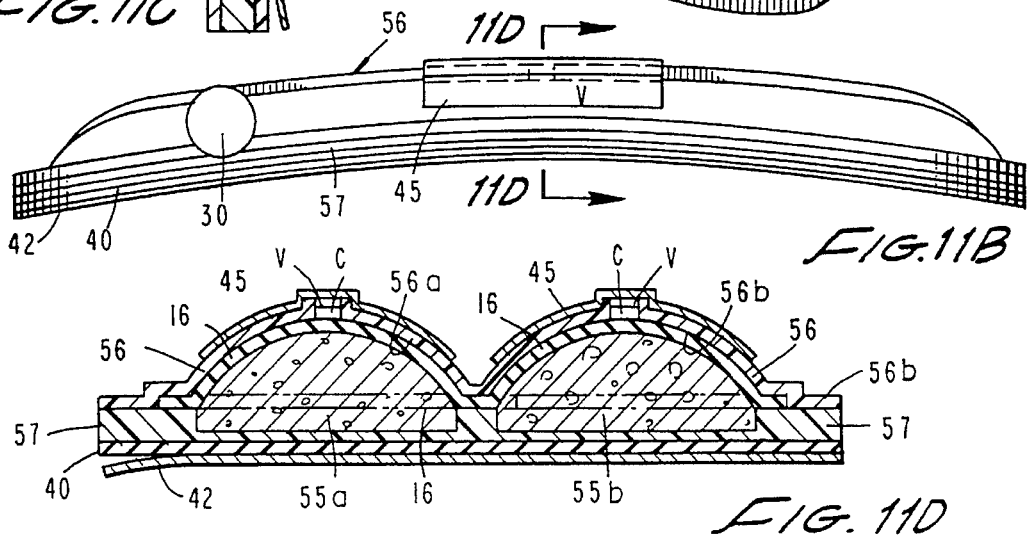
FIG. 11A
FIG. 11B
FIG. 11C
FIG. 11D

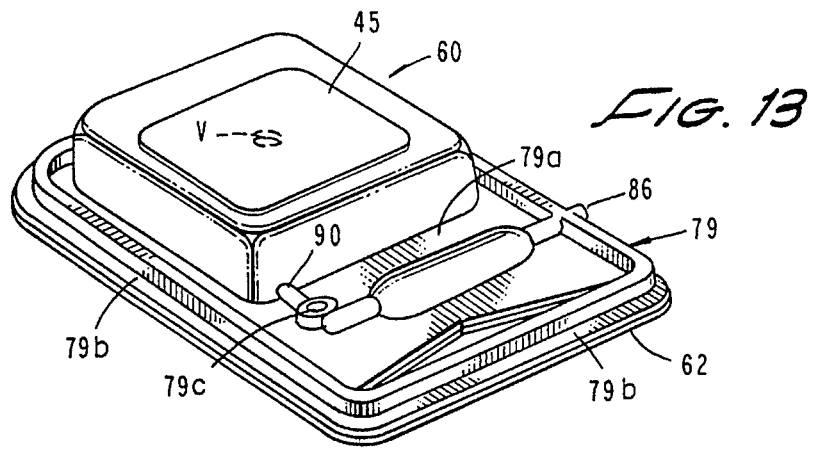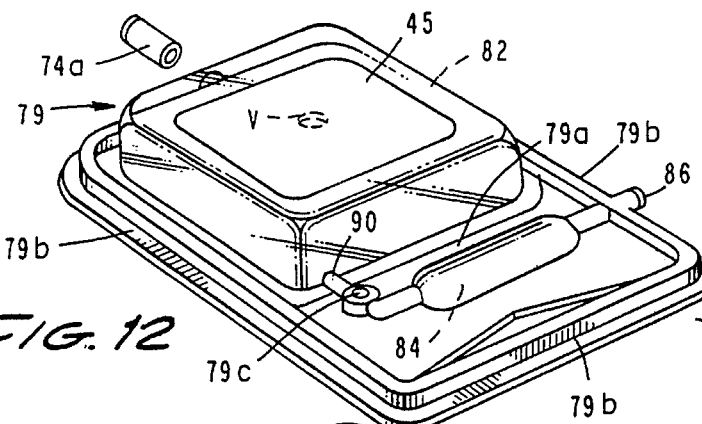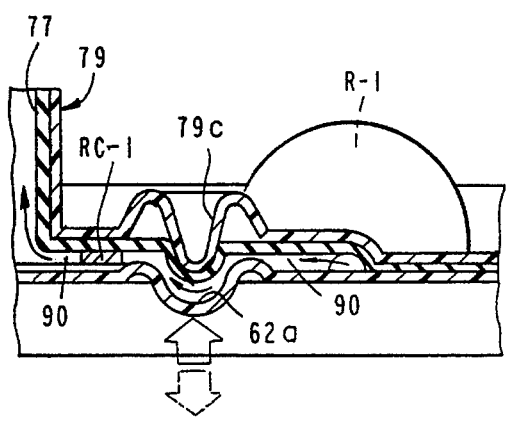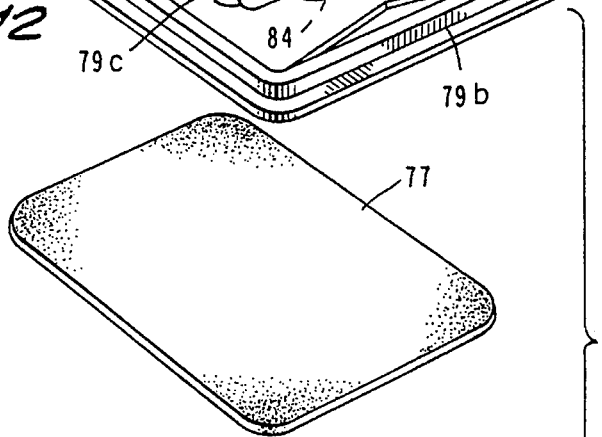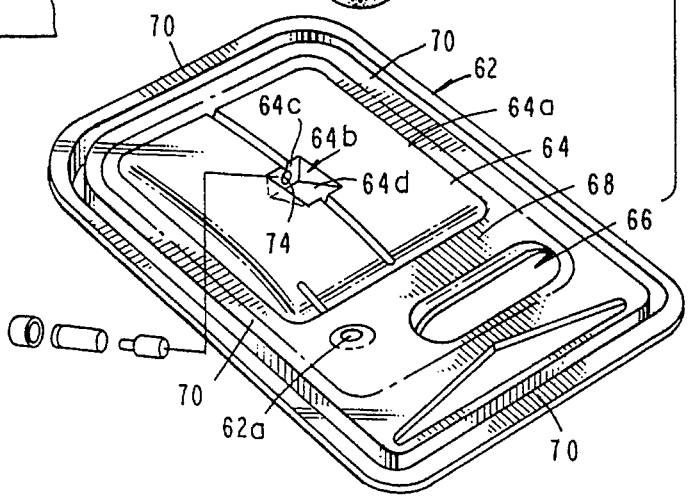

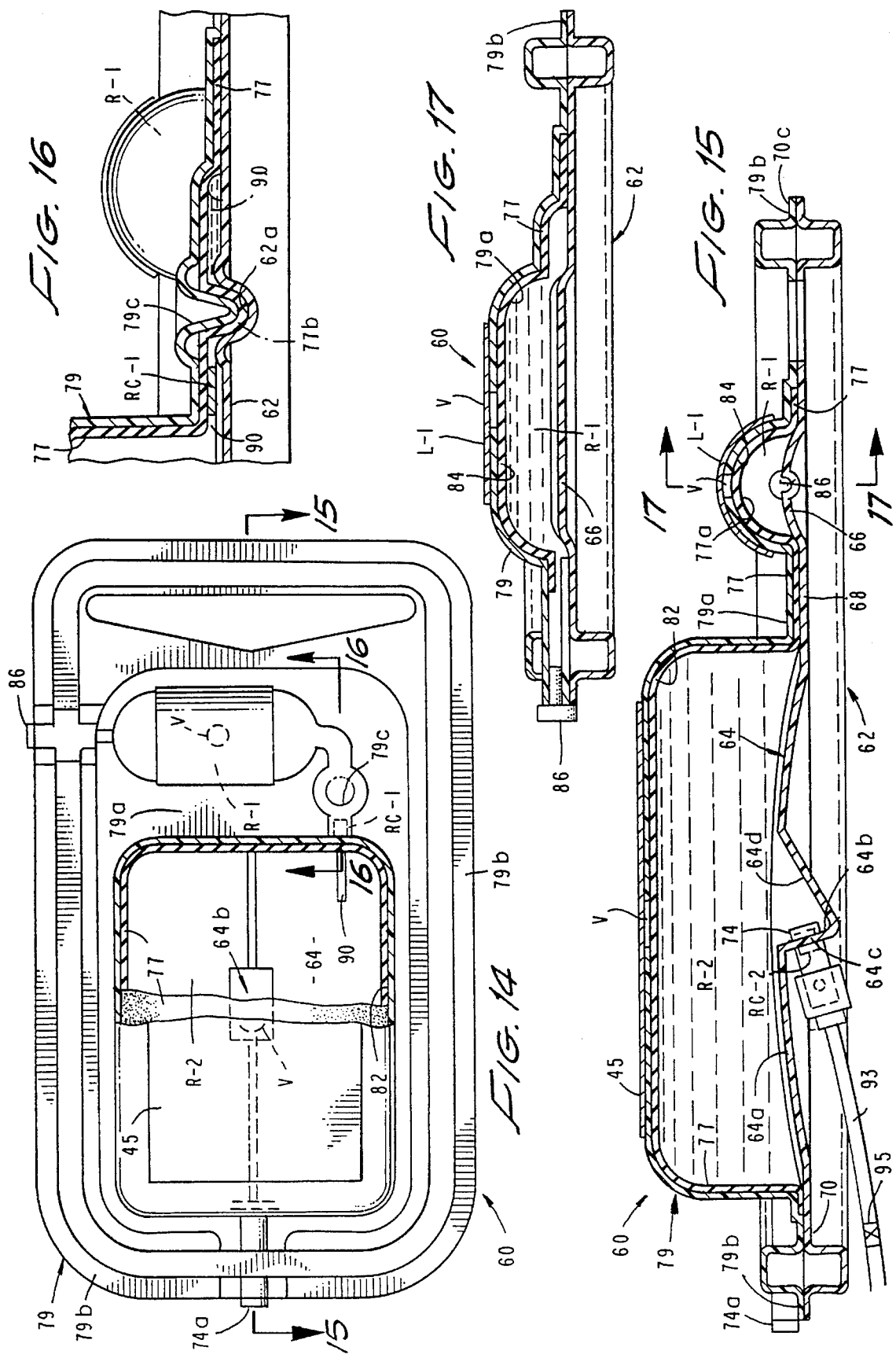

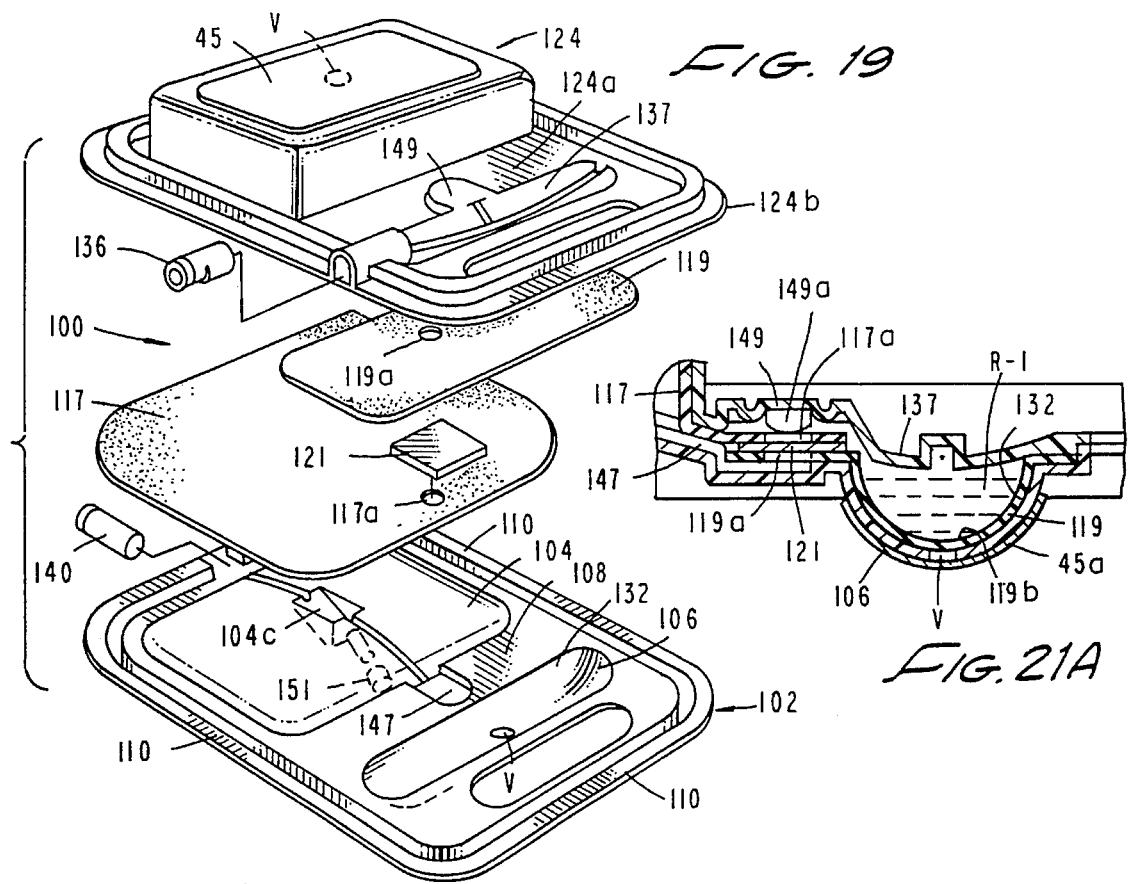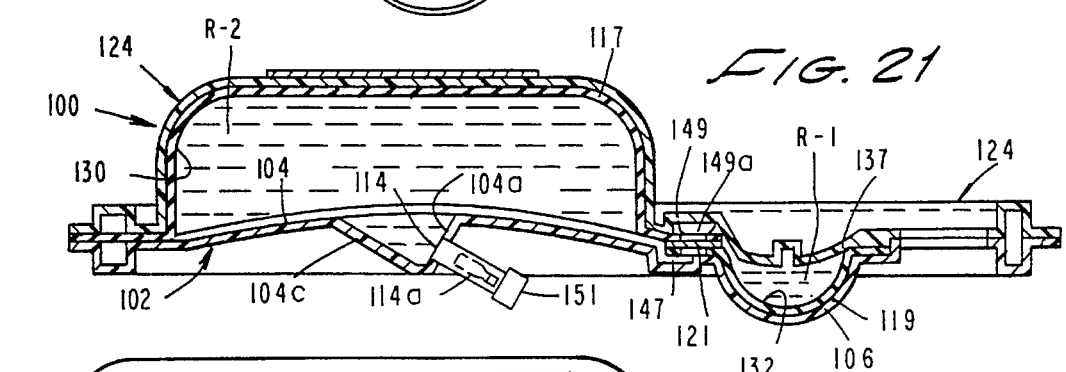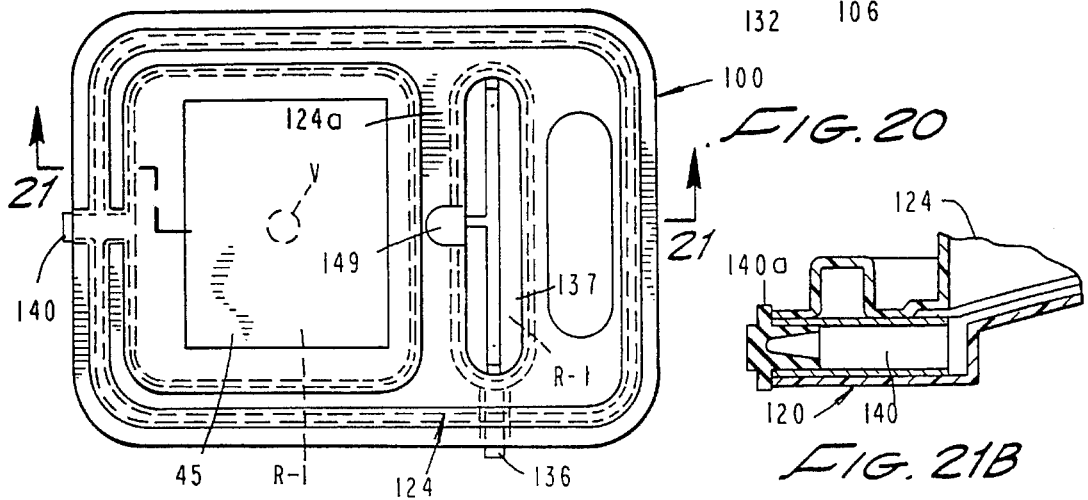

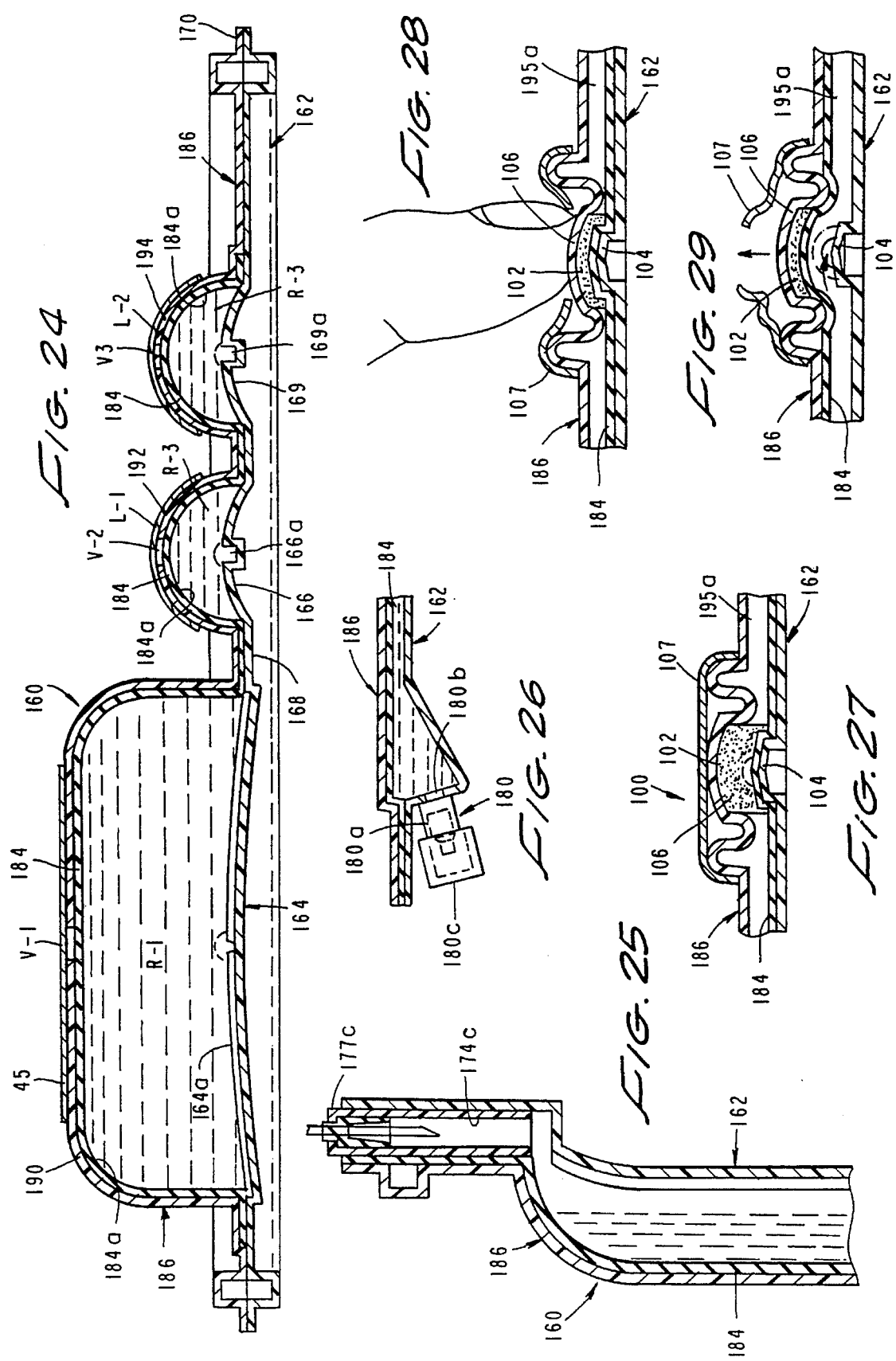

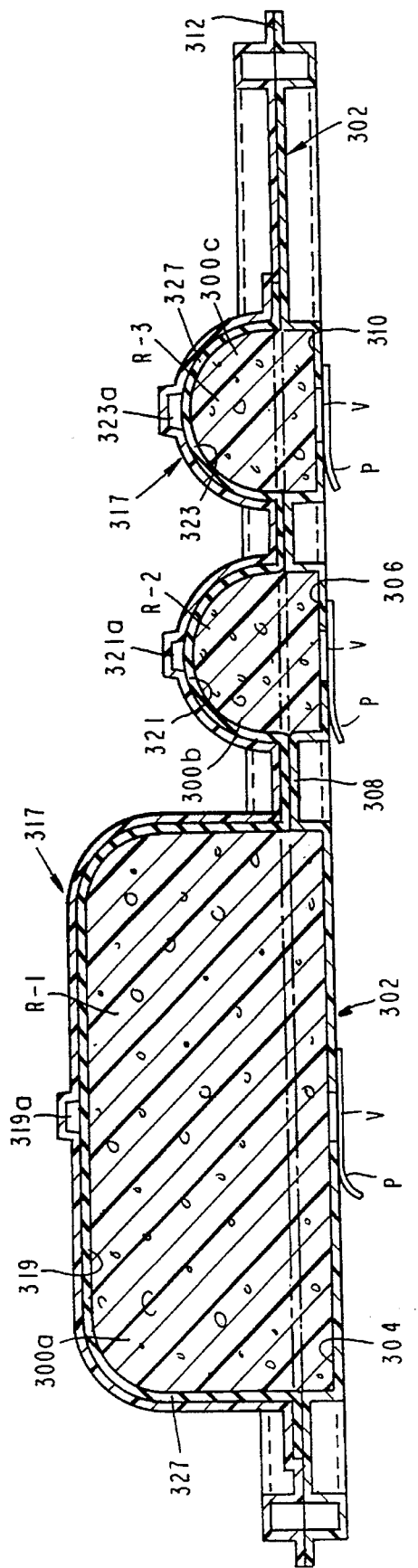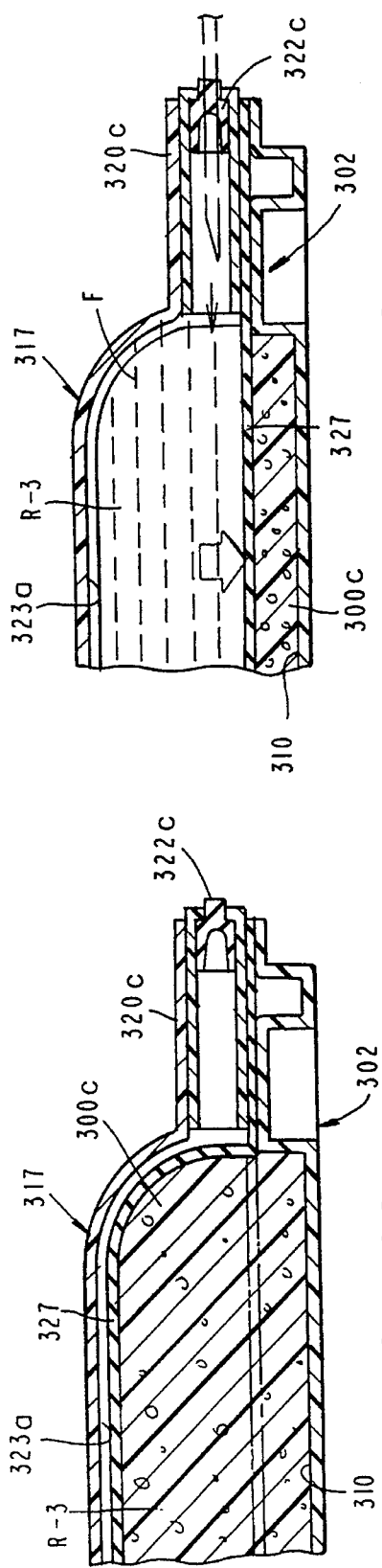
FIG. 32
FIG. 33A
FIG. 33

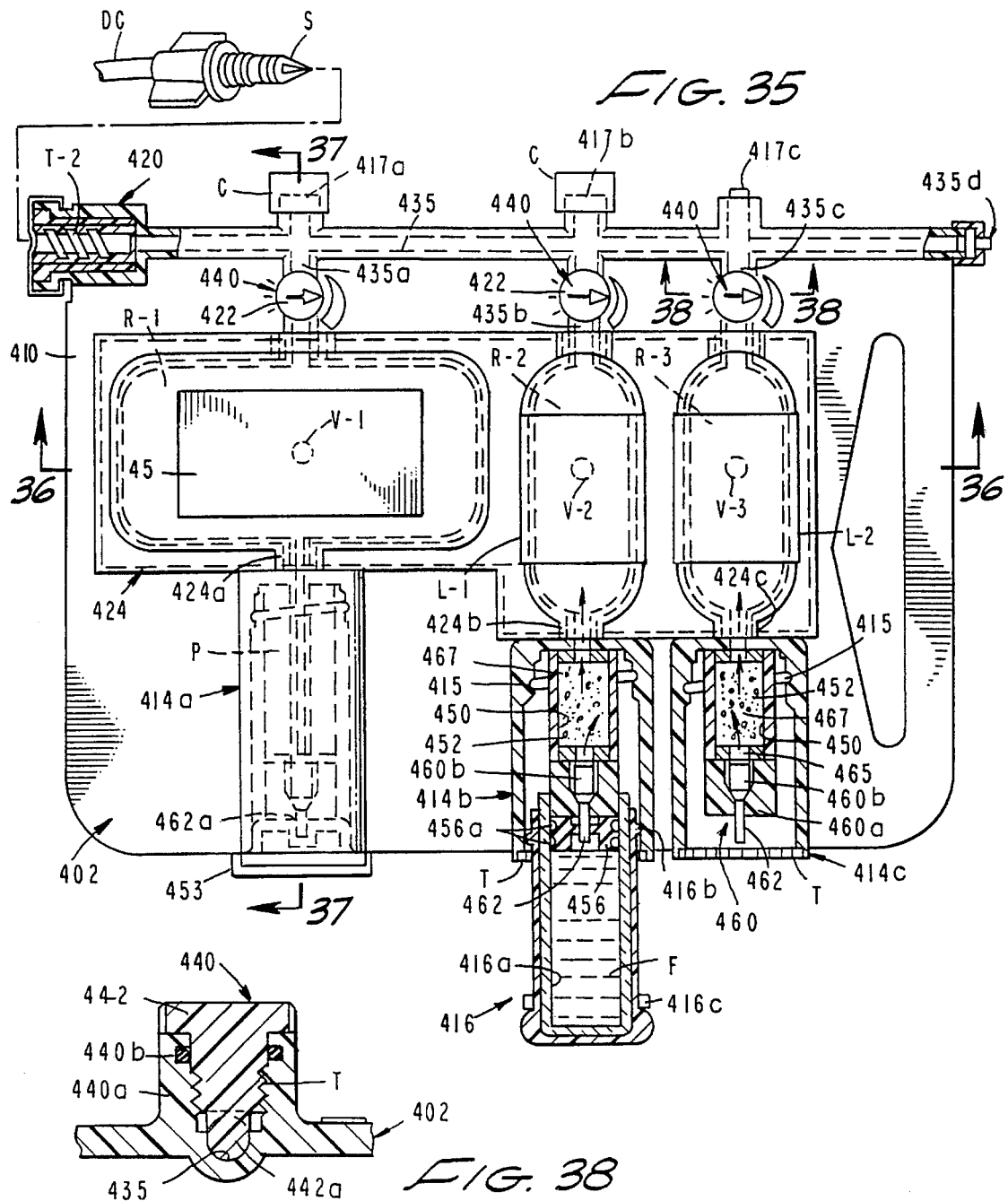
FIG. 35
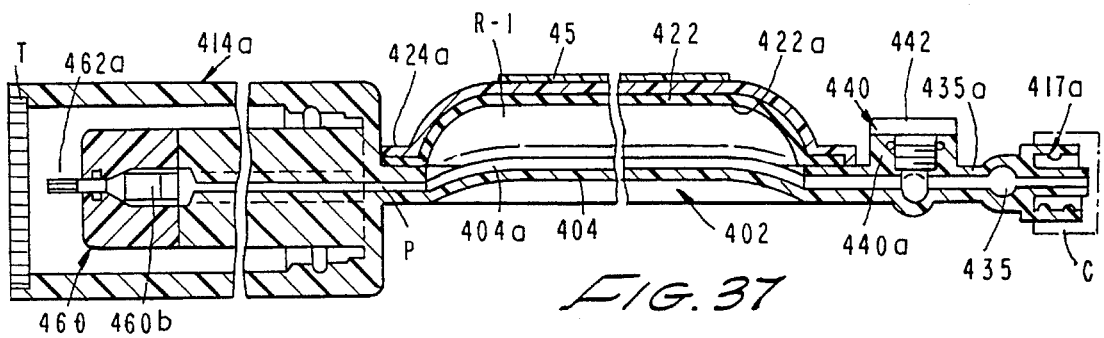
FIG. 38
FIG. 37

FLUID DELIVERY APPARATUS HAVING A STORED ENERGY SOURCE

This is a Divisional application of Continuation In Part application Ser. No. 08/069,937 filed May, 28, 1993 now U.S. Pat. No. 5,336,188 which is a Continuation In Part of Ser. No. 08/046,438, filed May 18, 1993 now U.S. Pat. No. 5,411,480 which is a Continuation In Part of application Ser. No. 07/870,021 filed Apr. 17, 1992 now U.S. Pat. No. 5,222,560 which was a continuation of application Ser. No. 07/870,269, filed Apr. 17, 1992 which has now issued into U.S. Pat. No. 5,205,820 and which is, in turn, a Continuation In Part of application Ser. No. 07/642,208, filed Jan. 16, 1991 which has now issued to U.S. Pat. No. 5,169,389 which is a Continuation In Part of application Ser. No. 07/367,304 filed Jun. 16, 1990 which has now issued to U.S. Pat. No. 5,019,047.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used as well as various alternate constructions of the apparatus of the invention are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/046,438 filed by the present inventor on Apr. 13, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the invention described in this Continuation-In-Part application comprises a rather large infusion device for infusing substantial quantities of fluids into the patient. The device in certain instances can be on the order of eight inches long and four inches wide and, therefore, cannot conveniently be attached to the arms or legs of the ambulatory patient. By providing a relatively soft, pliable device that has a unique, carefully engineered, curvilinear shape such as a kidney shape, a lenticular shape, a mesh of curves, a surface of revolution or any other shape that conforms to the anatomical configuration of the human body, proximate the point of infusion, the device can be comfortably and unobtrusively removably affixed to the patient's upper abdomen. In one form of this novel device, the stored energy source used to expel the fluid from the device comprises a unique expandable sponge-like member. In another form of the invention, the device uses a distendable membrane as the stored energy source.

Another novel form of the invention described in this Continuation-In-Part includes first and second cooperating fluid chambers both driven by unique stored energy sources. This embodiment of the invention permits two or more liquid components to be stored within the device and then controllable intermixed at the time of fluid delivery. Similarly, the multireservoir design permits flushing of one of the reservoirs and the cannula with any selected fluid.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

Another object of the invention is to provide an infusion device which embodies an expandable foam-like, stored-energy source that functions to precisely deliver medicinal fluids to a patient either at a fixed rate or at variable rates and one which is operational in all altitudes and attitudes.

Still another object of the invention is to provide an apparatus of the class described which is soft, conformable and compliant so as to readily conform to the patient's anatomy proximate the point of infusion. More particularly, one form of the invention is specially configured so that it can be unobtrusively removably connected to the patient's upper abdomen. The device of this form of the invention can be relatively large but, because of its unique footprint, can be worn by the ambulatory patient without discomfort.

Yet another object of the invention is to provide an apparatus as described in the preceding paragraph which is provided with a thin, flexible foam backing with adhesive for self-attachment so that the apparatus can be unobtrusively worn under clothing.

A further object of the invention is to provide a low profile, fluid delivery device of laminate construction which can be manufactured inexpensively in large volume by automated machinery.

Another object of the invention is to provide a device of the character described in which fluid is dispelled from the apparatus through either an integral infusion needle, or through a luer type connector, by a thin, distendable membrane cooperatively associated with a thin, plate-like base.

Another object of the invention is to provide an apparatus of the aforementioned character in which the expandable stored energy source is permeable to gases at least in one direction, whereby gases within the medicinal agent can be released from the fluid chamber and not injected into the patient.

A further object of the invention is to provide a fluid delivery device embodying an .expandable cellular mass which cooperates with a barrier member and a base to define a fluid chamber having a fluid outlet and in which the expandable cellular mass controllably urges fluid within the fluid chamber outwardly of the fluid outlet of the device.

Another object of the invention is to provide a fluid delivery device of the character described in the preceding paragraph in which the cellular mass comprises a compressible polymeric foam which functions to controllably expel fluid from the device at precise rate over a predetermined time period. Other objects of the invention are set forth in and will become apparent from a study of U.S. Pat. No. 5,205,820 which is incorporated herein.

BRIEF DESCRIPTION OF THE DRAWINGS

FIG. 1 is a generally perspective view of one form of the fluid dispensing apparatus of the invention.

FIG. 2 is a generally perspective view of the apparatus of FIG. 1 in an assembled configuration.

FIG. 3 is a top view of the apparatus.

FIG. 4 is a front view of the apparatus.

FIG. 5 is an enlarged cross-sectional view taken along lines 5—5 of FIG. 4.

FIG. 6 is a cross-sectional view similar to FIG. 5, but showing expansion of the expandable energy source member to expel fluid from the apparatus.

FIG. 7 is a cross-sectional view taken along lines 7—7 of FIG. 4.

FIG. 8 is a cross sectional view taken along lines 8—8 of FIG. 7.

FIG. 9 is a generally perspective exploded view of another embodiment of the fluid dispensing apparatus of the present invention.

FIG. 10 is a top view of the apparatus shown in FIG. 10 in an assembled configuration.

FIG. 11 is a cross sectional view taken along lines 11—11 of FIG. 10.

FIG. 11A is a generally perspective, exploded view of yet another form of the invention.

FIG. 11B is a top plan view of the device.

FIG. 11C is a longitudinal, cross-sectional view of the embodiment of FIG. 11B.

FIG. 11D is a cross-sectional view taken along lines 11D—11D of FIG. 11B.

FIG. 12 is a generally perspective exploded view of another embodiment of the apparatus of the present invention.

FIG. 13 is a generally perspective view of the assembled apparatus illustrated in FIG. 12.

FIG. 14 is a top plan view of the apparatus of this form of the invention partly broken away to show internal construction.

FIG. 15 is a cross-sectional view taken along lines 15—15 of FIG. 14.

FIG. 16 is an enlarged cross-sectional view taken along lines 16—16 of FIG. 14.

FIG. 17 is a cross-sectional view taken along lines 17—17 of FIG. 15.

FIG. 18 is a cross-sectional view similar to FIG. 17, but showing the closure indentation in a flow permitting configuration.

FIG. 19 is an exploded, generally perspective view of yet another embodiment of the invention.

FIG. 20 is a plan view of the apparatus partially broken away to show internal construction.

FIG. 21 is an enlarged cross-sectional view taken along lines 21—21 of FIG. 20.

FIG. 21A is an enlarged, fragmentary, cross-sectional view of one of the fluid reservoirs and fluid flow control means of the device.

FIG. 21B is an enlarged, fragmentary, cross-sectional view of the septal inlet port of the device.

FIG. 24 is a cross-sectional view taken along lines 24—24 of FIG. 23.

FIG. 25 is a cross-sectional view taken along lines 25—25 of FIG. 23.

FIG. 26 is a cross-sectional view taken along lines 26—26 of FIG. 23.

FIG. 27 is a cross-sectional view taken along lines 27—27 of FIG. 23.

FIG. 28 is a cross-sectional view similar to FIG. 27, but showing the closure mechanism in a depressed configuration.

FIG. 29 is a cross-sectional view similar to FIG. 28 but showing the closure mechanism in a released state.

FIG. 32 is a cross-sectional view taken along lines 32—32 of FIG. 31.

FIG. 33 is a cross-sectional view taken along lines 33—33 of FIG. 31.

FIG. 33A is a cross-sectional view similar to FIG. 33 but showing the stored energy means in a compressed state.

FIG. 35 is a plan view of the appratus partly broken away to show internal construction.

FIG. 37 is a cross-sectional view taken along lines 37—37 of FIG. 35.

FIG. 38 is a cross-sectional view taken along lines 38—38 of FIG. 35.

DESCRIPTION OF THE INVENTION

Figure 22:
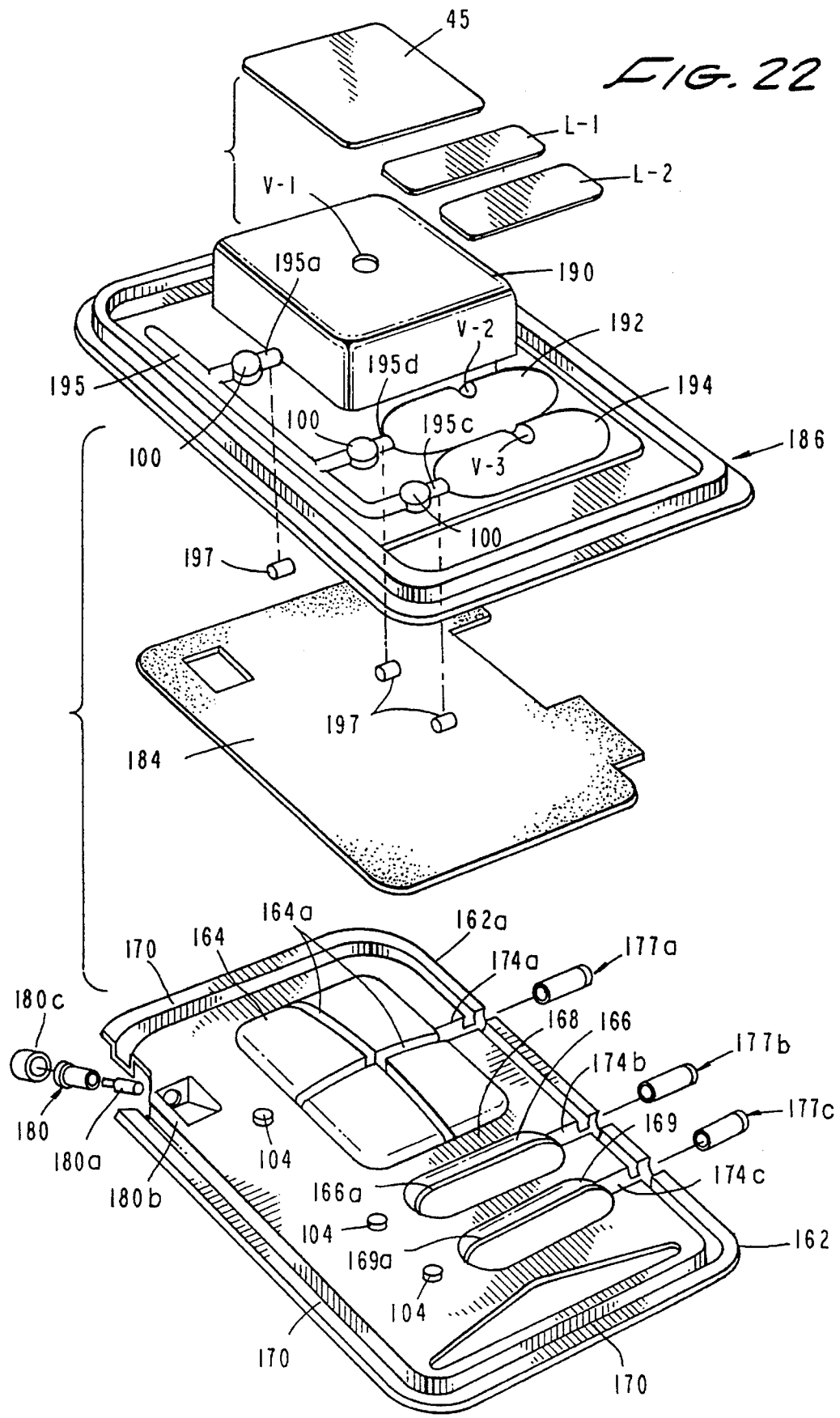
FIG. 22 is an exploded, generally perspective view of still another embodiment of the invention.

Referring to FIGS. 1 through 8, another embodiment of the invention is there shown. The apparatus of this form of the invention is similar in certain respects to the embodiments described in U.S. Pat. No. 5,205,820. However, the apparatus of this later form of the invention is of a very simple construction, exhibits a unique configuration and includes a novel expandable sponge-like cellular member which functions as the stored energy source for controllably expelling beneficial agents from the device.

Turning particularly to FIG. 1, the apparatus can be seen to comprise a base 12 having a novel curvilinear or kidney like geometry and an operating assembly 14 associated therewith. Operating assembly 14 comprises a thin planar barrier member 16 and a stored energy source, shown here as an expandable sponge like member 18. A cover 20 having an internal chamber 20a and a base flange 20b cooperates with base 12 to enclose the operating assembly in the manner shown in FIG. 5.

A combination filling means and fluid outlet means is provided on base 12 and is used to fill the fluid reservoirs "R" via flow passageways 21 and ports 21a and 21b provided in base 12 (FIGS. 5 and 7) with either a beneficial agent or parenteral fluid. After the reservoirs are filled, the inlet port 22 of the filling means is closed by a check valve 24 of the character illustrated in FIG. 7. Valve 24 acts against a valve seat 26 formed in an outlet fitting, such as a luer fitting 28 which is affixed to base 12. A removable cap 30 normally seals fitting 28. As shown in FIG. 8, fitting 28 is provided with a plurality of circumferentially-spaced, axially-extending flow passageways 29 within which valve member 24 is centered. Passageways 29 communicate with flow passageway 21 to permit the flow of fluid into and out of reservoirs R.

Base member 12 includes integrally formed barrier member engagement means, or ullage means shown here as a pair of upstanding curved protuberances 34. Each of the curved protuberances 34 is provided with a longitudinally extending first fluid passageway or conduit 36. When the apparatus is assembled in the manner shown in FIG. 7, passageways 36 are superimposed over and communicate with passageway 21. As indicated in FIGS. 5 and 7, protuberances 34 extend upwardly into fluid chambers R so as to define an ullage within the chambers. Protuberances 34 can be integrally formed with base 12 or can be attached thereto for certain applications.

Affixed to the bottom of base 12 is a cushioning means shown here as a thin, planar shaped foam pad 40. Foam pad 40 is provided with adhesive on both its upper and lower surfaces. the adhesive on the upper surface of pad 40 enables the pad to be affixed to the lower surface of base 12. As indicated in FIGS. 1 and 2, a peel strip 42 is connected to the bottom surface of foam pad 40 by the adhesive provided thereon. When the device is to be used, peel strip 42 can be stripped away from pad 40 so that the adhesive on the lower surface of the foam pad 38 can be used to releasably affix the apparatus of the invention to the patient's skin proximately the upper abdomen. The unique shape of the device coupled with its flexibility permits it to comfortably conform to the patient's body.

The various materials that can be used to construct the various components of the device, including the base member, the barrier member, the stored energy source and the cover are discussed in detail in Ser. No. 08/046,438 which is incorporated herein by reference With the check valve having been opened by a suitable dispensing connector of a character well known in the art, fluid is first introduced into the fluid chambers R via the luer fitting and passageways 21 and 36. During the fluid dispensing step, as expandable sponge-like member 18 attempts to return to its original less compressed configuration (FIG. 6), it will force barrier member 16 to move toward engagement with the upper surface of protuberances 34 and in so doing will cause barrier member or membrane 16 to efficiently expel the fluid contained within the reservoirs from the device via passageways 36 and 21.

The configuration of protuberances 34 ensure that substantially all of the fluid within chambers R will be expelled therefrom as the expandable member returns toward its starting, uncompressed configuration. Expandable member 18 can be constructed of various materials and be configured to provide various degrees of expansion rate so as to control the rate of its return to its less compressed state thereby controlling the rate of fluid expulsion.

Cover 20 is preferably constructed from a yieldably deformable moldable plastic and can include venting means, or apertures V, for venting gases, if any, contained within the medicinal agent. Affixed to the top of cover 20 is a medicant and use instruction label 45 which overlays apertures V and can be used to identify the medicinal fluid contained within chambers R of the device.

Turning now to FIGS. 9 through 11, yet another form of the apparatus of the invention is there shown. The device of this form of the invention is similar in most respects to the embodiment shown in FIGS. 1 through 8, save that the stored energy source is not a cellular, elastomeric mass, but rather comprises a distendable membrane 50. Membrane 50 functions as the stored energy source in much the same way as do the distendable membrane constructions disclosed in U.S. Pat. No. 5,205,820 which is incorporated herein by reference.

In this latest form of the invention, the operating assembly comprises the distendable membrane 50 which overlays base 12. Base 12 is of the character previously described and like membrane 50 is generally kidney shaped. Disposed between membrane 50 and cover 20 is a semi-rigid, porous structure 52 which, as best seen in FIG. 11, includes concave portions 54 having interior surfaces against which membrane 50 expands as it distends into its extended configuration. As before, as membrane 50 is distended from the first position shown in FIG. 11 to a position wherein it is in engagement with the interior walls of concave portions 54, internal stresses are built up which tend to return it toward its original non-distended configuration.

Suitable materials for the construction of membrane 50 and the manner in which the membrane functions are discussed in greater detail in co-pending application Ser. No. 08/046,438.

Cover 20 cooperates with base 12 to enclose the operating assembly in the manner shown in FIG. 11 and is provided with combination filling means and fluid outlet means for filling the fluid reservoirs R via flow passageways 21 provided in base 12 (FIGS. 5 and 7). After the reservoirs are filled, the inlet port 22 of the filling means is closed by a check valve 24 of the character illustrated in FIG. 7. As before, valve 24 acts against a valve seat 26 formed in an outlet fitting, such as a luer fitting 28. A removable cap 30 normally seals fitting 28.

Materials suitable for the construction of distendable membrane 50 and porous structure 52 are identified in U.S. Pat. No. 5,205,820 which is incorporated herein by reference.

In operation of the device, fluid is introduced into the fluid chambers R via the luer fitting and passageways 21 and 36 causing membrane 50 to distend into concave portions 54. During the fluid dispensing step and with the check valve suitably opened by an interacting dispensing connector of a character well known in the art, as distendable membrane 50 attempts to return to its original non-distended configuration (FIG. 11), it will move toward engagement with the upper surface of protuberances 34 and in so doing will controllably expel the fluid contained within the reservoirs from the device via passageways 36 and 21.

As best seen in FIG. 2, external flow rate control means R-C are provided in infusion line L and function to precisely control the rate of fluid flow toward the patient. As also indicated in FIG. 2, porous structure 52, like sponge member 18, is of a character that, in cooperation with cover 20, will function as venting means including apertures V for venting gases, if any, which are contained within the medicinal agent. Affixed to the top of cover 20 is a medicant and use instruction label 45 which may be breathable and covers apertures V and can be used to identify the medicinal fluid contained within chambers R of the device.

As was the case with the previously described embodiment, the unique shape of the device coupled with its flexibility permits it to comfortably conform to the patient's body. When worn under clothing, the device will not create an unsightly bulge thereby making it ideally suited for use by ambulatory patients.

Referring to FIGS. 11A through 11D, still another embodiment of the invention is there shown. The apparatus of this form of the invention is similar in many respects to the embodiment shown in FIGS. 1 through 8 and like numbers are used to identify like components. This latest form of the invention also uses an expandable sponge-like assembly 55 as the stored energy source. However, here the position of the stored energy source and the barrier membrane are reversed so that the fluid within the internal reservoir is visible through the transparent cover member 56. Assembly 55 is here made up of two separate cellular sponge-like members 55a and 55b.

Turning particularly to FIG. 11A, the apparatus of this form of the invention can be seen to comprise a base 57 having a novel curvilinear or kidney like geometry and an operating assembly associated therewith. The operating assembly here comprises a thin planar barrier member 16 which cooperates with the previously identified stored energy source, or expandable sponge-like assembly 55. Cover 56 is provided with an internal chamber 56a and a base flange 56b which cooperates with base 57 to enclose the operating assembly in the manner shown in FIGS. 11C and 11D.

As before, combination filling means and fluid outlet means is provided on base 57 and is used to fill the fluid reservoirs "R" via flow passageways 58 provided in base 57 (FIG. 11C) with either a beneficial agent or parenteral fluid. After the reservoirs are filled, the inlet port "IP" of the filling means is closed by a check valve 24 of the character previously described. Valve 24 acts against a valve seat 26 formed in an outlet filling, such as a luer filling 28 which is affixed to base 57. A removable cap 30 normally seals fitting 28. As before, fitting 28 is provided with a plurality of circumferentially-spaced, axially-extending flow passageways 29 within which valve member 24 is centered (see FIG. 8).

In this latest embodiment, cover member 56 rather than the base member, includes integrally formed barrier member engagement means, shown here as a pair of side by side chambers 59a and 59b. Each of the chambers is provided with a longitudinally extending first fluid passageway or conduit "C". When the apparatus is assembled in the manner shown in FIG. 11C, conduits "C" are superimposed over and communicate with reservoirs "R".

Affixed to the bottom of the base 57 is a cushioning means shown here as a thin, planar shaped foam pad 40. A peel strip 42 is connected to the bottom surface of foam pad 40 by the adhesive provided thereon. When the device is to be used, peel strip 42 can be stripped away from pad 40 so that the adhesive on the lower surface of the foam pad can be used to releasably affix the apparatus of the invention to the patient's skin proximately the lower abdomen. Once again, the unique shape of the device coupled with its flexibility permits it to comfortably conform to the patient's body.

With the check valve having been opened by a suitable dispensing connector of a character well known in the art, fluid is first introduced into the fluid chambers "R" via the luer fitting and passageways 58. During the filling step, expandable sponge-like members 55a and 55b are forced by barrier member 16 to move from the extended position shown in FIGS. 11C and 11D into a more compressed configuration. During the dispensing step, members 55a and 55b force barrier member 16 to move from the position shown by the phantom lines in FIGS. 11C and 11D outwardly and in so doing cause barrier member or membrane 16 to efficiently expel the fluid contained within the reservoirs from the device via conduits C and passageways 58.

The configuration of chambers 56a and 56b ensure that substantially all of the fluid within chambers "R" will be expelled therefrom as the expandable members return toward their starting, less compressed configuration shown in the drawings. As previously mentioned, cover member 56 is constructed of materials which are substantially transparent so that the fluid contained within filled reservoirs "R" is visible to the user of the device at the time of infusion or fluid expulsion.

Referring to FIGS. 12 through 18, another embodiment of the invention is there shown. The apparatus of this form of the invention is similar in certain respects to the last described embodiment. However, the apparatus of this later form of the invention uniquely includes first and second spaced apart reservoirs with first and second liquid components being contained within the reservoirs.

Turning particularly to FIGS. 12 and 13, the apparatus of this latest form of the invention, which is generally designated by the numeral 60, can be seen to comprise a base 62 having a first portion 64, a second portion 66, a third portion 68, which is disposed intermediate portions 64 and 66, and a fourth marginal portion 70 which circumscribes the first, second and third portions. Base 62 is preferably constructed of a thin moldable thermo plastic material which can be thermo formed into the cross-sectional configuration shown in FIG. 15. More particularly, first portion 64 of the base is molded so as to have an upstanding central portion 64a which is provided proximate its center with a depression 64b. Depression 64b is defined by intersecting angularly extending walls 64c and 64d. Provided in wall 64c is a fluid inlet 74. As best seen in FIG. 15, intermediate portion 68 as well as marginal portion 70 is generally flat.

Overlying base 62 is a distendable member shown here as an elastomeric, generally planar distendable membrane 77. Superimposed over base 62 and membrane 77 in a membrane clamping relationship is a formed cover means, or cover assembly 79 which is also preferably constructed of a heat formable thermo plastic material. It is to be understood that both base 62 and cover assembly 79 can be constructed from a wide variety of materials and can be sealably interconnected with membrane 77 in a number of ways well known in the art including mechanical, adhesive and thermo bonding. Affixed to the cover member is a use and instruction label 45 of the character previously described (FIG. 14). When cover means 79 is interconnected with base 62 in the manner shown in FIG. 13, the cover means sealably encapsulates membrane 77. More particularly, as best seen in FIG. 15, the central portion 79a of cover 79 clamps and seals membrane 77 securely against the third intermediate portion 68 of base 62. In similar fashion, the marginal portion 79b of cover 79 sealably clamps the marginal portions of membrane 77 against the fourth marginal portion of base 62 which circumscribes portions 64 and 66.

Referring both to FIGS. 12 and 15, it can be seen that the cover member 79 is provided with a first reservoir defining chamber 82 which is superimposed over portion 64 of base 62 and a second reservoir defining chamber 84 which is disposed over second portion 66 of base 62. In the manner presently to be described, the inner walls of these chamber-defining portions provide engagement surfaces for engagement by distendable membrane 77 when the membrane is distended from a first position in which it is proximate base 62 to a second distended position in which the membrane moves proximate the interior walls of chamber defining portions 82 and 84 of cover 79. As illustrated in FIGS. 12 and 15, cover 79 is provided with a fluid inlet port 86 which communicates with the interior of a reservoir R-1. Reservoir R-1 is formed between portions 66 of base 62 and the interior surface 77a of membrane 77. In similar fashion, when the membrane is in a further distended configuration, the membrane cooperates with first portion 64 of base 62 to define a second reservoir R-2. With this construction, reservoir R-2 can be filled via septal port 74a. As fluid flows into the reservoir, distendable membrane 77 will be distended from the first position wherein it is in engagement with the base to the second position shown in FIG. 15 wherein it cooperates with the base to define reservoir R-2. In similar fashion, fluid can be introduced through septal port 86 to move the distendable membrane from a first position in engagement with portion 66 of base 62 into the second position shown in FIG. 15 wherein it cooperates with the base to define reservoir R-1.

Reservoirs R-1 and R-2 can communicate with each other via a fluid passageway 90 that is provided in cover 79. As indicated in FIG. 16, passageway 90 is normally closed by a downwardly deformed generally frustoconically shaped wall section 79c provided in cover member 79. This deformed wall section is closely received within a generally hemispherically shaped depression 62a formed in base 62. When wall section 79c is in its deformed configuration, a small section 77b of membrane 77 is sealably clamped against the interior wall of depression 62a in a manner to prevent fluid flow through passageway 90.

Turning now to FIG. 18, it is to be noted that an upward manual pressure exerted on the exterior wall of depression 62a in the direction of the solid line arrow in FIG. 18, will cause deformed wall section 79c of the cover means to move upwardly from the first position shown in FIG. 17 to the second position shown in FIG. 18 thereby opening passageway 90 to fluid flow. When passageway 90 is in the open or fluid flow configuration, fluid can flow freely from reservoir R-1 to reservoir R-2.

By way of example, in using the device of this latest form of the invention, reservoir R-2 is filled with a first fluid component by means of a fluid conduit 93 which is interconnected with fluid inlet 74 (FIG. 15). As fluid flows into inlet 74, distendable membrane 77 will be distended into the configuration shown in FIG. 15 thereby filling reservoir R-2 with the first liquid component. Reservoir R-1 can be filled with a second fluid component by introducing the second fluid component into fluid inlet 86 provided in cover 79. As the second component flows into inlet 86, it will distend the distendable membrane 77 into the distended configuration shown in FIG. 15 thereby filling reservoir R-1 with the second component. Membrane 77 can be specifically tailored so as to provide differential stresses and differential areas of stored energy densities as between reservoirs R-1 and R-2 and thereby enabling fluid flow between the reservoirs. Initially fluid cannot flow between reservoirs R-1 and R-2 because of the closure means which is here provided in the form of the deformable wall section 79c of cover 79.

When it is desired to intermix the fluids within R-1 and R-2, an upward pressure is exerted against the external surface of depression 62a formed in the base. This causes wall section 79c to move upwardly in the manner shown in FIG. 18 so as to open passageway 90 to fluid flow in the manner shown in FIG. 18. With the passageway open, fluid under pressure within chamber R-1 can rapidly flow into partially filled reservoir R-2 via rate control means RC-1 and intermix with or provide a washing action to the fluid component contained within reservoir R-2. After the fluid components, which may be beneficial agents of the character defined in U.S. Ser. No. 08/046,438, have been intermixed, conduit 93, which has been closed by a standard closure clamp or other valve means 95 of a character well known to those skilled in the art, is opened permitting the intermixed fluid now contained within reservoir R-2 to flow outwardly of the device via rate control RC-2 through conduit 93. Rate control means RC-1 and RC-2 can comprise hydrophillic porous masses of a character well known in the art.

In addition to using the device of this latter form of the invention for fluid mixing and simultaneous delivery of first and second components, the device can also be used for sequentially delivering the first and second components.

Turning now to FIGS. 19 through 21, yet another embodiment of the invention is there shown and generally designated by the numeral 100. The apparatus of this form of the invention is very similar in construction to the last described embodiment and like components are identified with like numbers. However, the apparatus of this later form of the invention embodies a slightly different closure means for controlling fluid flow through the fluid passageway that connects the two reservoirs of the apparatus. Superimposed over portion 110 of base 102 is a first elastomeric membrane 117. Superimposed over portion 106 of base 102 is a second elastomeric generally planar distendable membrane 119 which is somewhat smaller that membrane 117. Membranes 117 and 119, which may have different operating characteristics, are provided with indexable apertures 117a and 119a respectively. Disposed intermediate and sealably affixed to membranes 117 and 119 and covering the apertures therein, is a frangible membrane 121, the purpose of which will presently be described.

Superimposed over base 102 and membranes 117, 119 and 121 is a formed cover means, or cover assembly 124 which is also a preferably constructed of a heat formable thermo plastic material. When cover means 124 is interconnected with base 102 in the manner shown in FIG. 21, the cover means sealably encapsulates the membranes. More particularly, as best seen in FIGS. 19 and 21, the central portion 124a of cover 124 clamps membranes 117 and 119 securely against the third intermediate portion 108 of base 102. In similar fashion, the marginal portion 124b of cover 124 sealably clamps the marginal portions of the membranes against the fourth marginal portion of base 102 which circumscribes portions 104 and 106. Once again, the cover means and base can be sealably interconnected with the membranes by various mechanical, bonding and thermo welding techniques. Cover assembly 124 is also provided with suitable vent means for venting reservoirs R-1 and R-2. As before, the vent means are covered by a breathable, hydrophobic medicament and use label 45 and a cover patch 45a (see FIG. 21A).

Referring both to FIGS. 19 and 21, it can be seen that the cover member 124 is provided with a first reservoir defining chamber 130 which is superimposed over upraised portion 104 of base 102. A second reservoir defining chamber 132 is formed in base 102 below second portion 106. In the manner presently to be described, the inner walls of these two chamber-defining portions provide engagement surfaces for engagement by distendable membranes 117 and 119 when the membranes are distended from a first planar position to a second more distended position in which the membranes move into proximity with the interior walls of chamber defining portions 130 and 132.

As illustrated in FIG. 20, cover 124 is provided with a fluid inlet port 136 which comprises a septal port of standard design which is selably connected to cover 124 and base 102 and communicates with the interior of a reservoir R-1. Reservoir R-1 is formed between a top wall portion 137 of cover 127 (FIG. 19) and the interior surface 119a of membrane 119. In similar fashion, when membrane 117 is in its more distended configuration, the membrane cooperates with first portion 104 of base 102 to define a second reservoir R-2. With this construction, reservoir R-2 can be filled through an inlet port 140 which is sealably connected to base 102 and which, as shown in FIG. 21B, comprises a septal port 140a pierceable by either a needle or a blunt cannula. As fluid flows into this inlet port, distendable membrane 117 will be further distended from the first position wherein it is in engagement with the base to the second position shown in FIG. 21 wherein it cooperates with the base to define reservoir R-2. In similar fashion, fluid can be introduced through inlet port 136 to move distendable membrane 119 from a first generally planar position into the second position shown in FIG. 22 wherein it cooperates with the cover to define reservoir R-1.

Reservoirs R-1 and R-2 can communicate with each other via a fluid passageway 147 (FIG. 21) that is provided between base 102 and cover 124. However, passageway 147 is normally closed by frangible membrane 121 which covers apertures 117a and 119a and blocks fluid flow therethrough. Turning to FIGS. 19 and 20, it is to be noted that cover 124 is provided with an upstanding push button like protuberance 149 which is disposed directly over frangible membrane 121. When a downward pressure is exerted on protuberance 149, frangible membrane 121 will be ruptured by member 149a (see FIG. 21A) thereby permitting fluid to flow freely through passageway 147 from reservoir R-1 to reservoir R-2.

In using the device of this latest form of the invention, reservoir R-2 can be partially filled with a first fluid component via inlet 140 (FIG. 20). As fluid flows into inlet 140, distendable membrane 117, which can have a first operating characteristic, will be distended part way into chamber 130 thereby partially filling reservoir R-2 with the first component. Reservoir R-1 can be filled with a second fluid component by introducing the second fluid component into fluid inlet 136 provided in cover 124. As the second component flows into inlet 136, it will distend the distendable membrane 119 which can have a second operating characteristic, downwardly into the distended configuration shown in FIG. 21 thereby filling reservoir R-1 with the second component. Initially fluid cannot flow between reservoirs R-1 and R-2 because of the closure means which is here provided in the form of frangible membrane 121.

When it is desired to intermix the fluids within R-1 and R-2, a downward pressure is exerted against protuberance 149. This causes member 149a to rupture frangible membrane 121 thereby permitting fluid to flow through apertures 117a and 119a. With the indexed apertures opened to fluid flow, fluid under pressure within chamber R-1 can rapidly flow into reservoir R-2 and intermix with the fluid component contained within reservoir R-2. The operating characteristics of membrane are designed so that the fluid flowing from reservoir R-1 toward reservoir R-2 will be of sufficient pressure to further distend membrane 117 into chamber 130 as the fluids are intermixed. A third fluid component can now be introduced into reservoir R-2 via either septal port 136 or 140 and intermixed with the first and second previously mixed components. This step further distends membrane 117 to the position shown in FIG. 21.

After the fluid components, which may be medicaments, parenteral liquids, enteral liquids, or beneficial agents of the character as defined in U.S. Ser. No. 08/046,438, have been intermixed, outlet 114, which has been closed by a cap 151 (FIG. 19) and by a standard check valve 114a of a character well known to those skilled in the art, can be opened. With outlet 114 open to fluid flow, the intermixed fluid now contained within reservoir R-2 can freely flow outwardly of the device as a result of the action of the second stored energy source or distended membrane 117.

Turning now to FIGS. 22 through 29, yet another embodiment of the invention is there shown. The apparatus of this form of the invention is similar in some respects to the last described embodiment. However, the apparatus of this later form of the invention uniquely includes first, second and third spaced-apart reservoirs that may contain first and third liquid components that may be intermixed for simultaneous delivery or they may be sequentially delivered for certain types of treatment.

Figure 23:
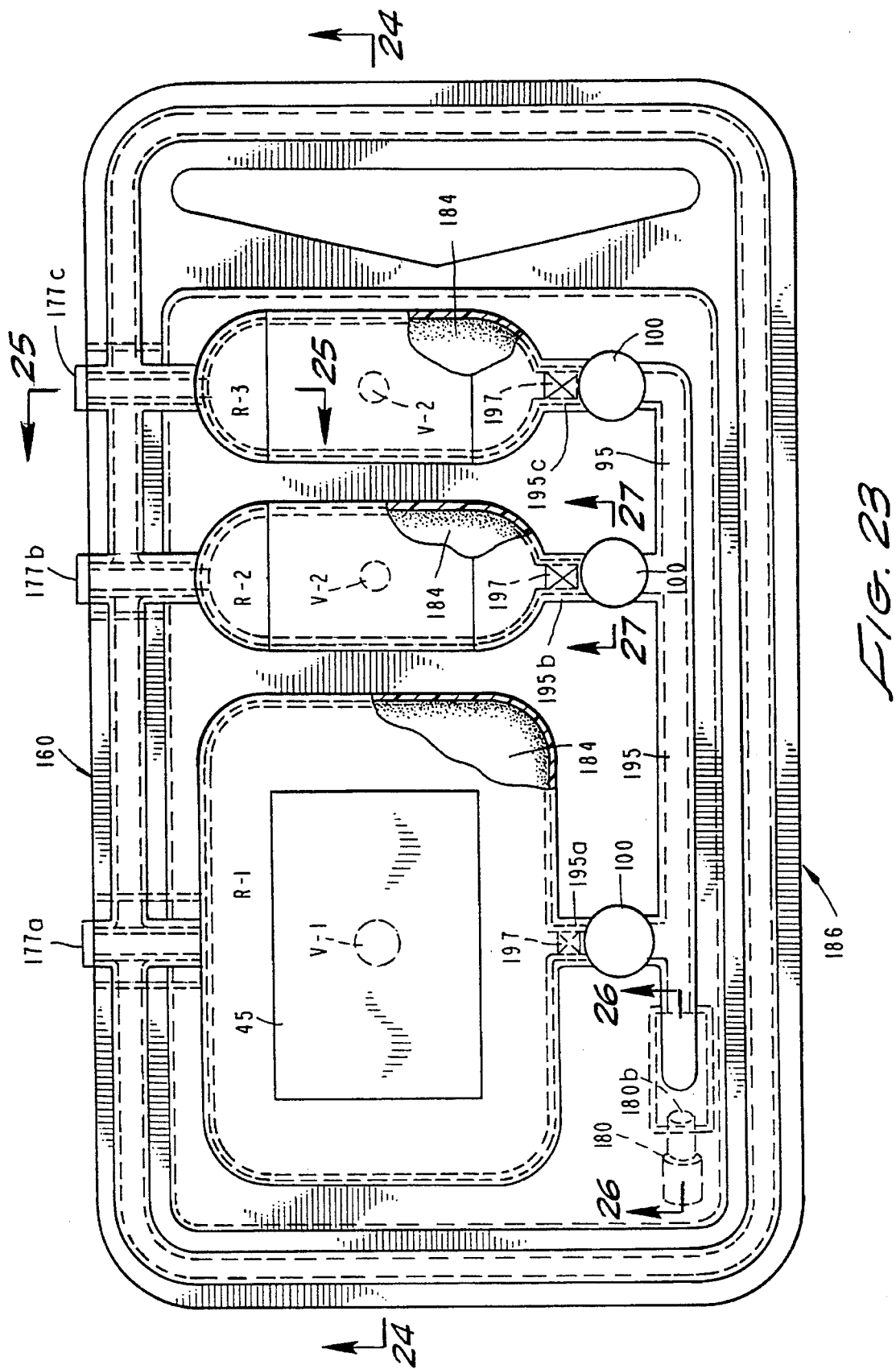
FIG. 23 is a plan view of the apparatus partially broken away to show internal construction.

Turning particularly to FIGS. 22, 23 and 24, the apparatus of this latest form of the invention, which is generally designated by the numeral 160, can be seen to comprise a base 162 having a first portion 164, a second portion 166, a third portion 168, which is disposed intermediate portions 164 and 166, a fourth portion 169 and a fifth marginal portion 170 which circumscribes the first, second, third and fourth portions. As before, base 162 is preferably constructed of a thin moldable thermo plastic material which can be thermo formed into the cross-sectional configuration shown in FIG. 24. More particularly, first, second and fourth portions 164, 166 and 169 of the base are molded so as to have upstanding central portions which are provided with fluid passageways 164a, 166a and 169a respectively. Provided in side wall 162a of base 162 are fluid inlets comprising channels 174a, 174b and 174c which are adapted to sealably receive fill port means for filling the reservoirs of the device in a manner presently to be described. The fill port means are here shown as septum assemblies 177a, 177b and 177c of standard construction (see also FIG. 25). As best seen in FIG. 24, the portion intermediate of portions 164 and 166 and the portion intermediate of portions 166 and 169, as well as marginal portion 170, are generally flat. Base 162 is provided with a dispensing means or outlet port assembly 180, the configuration of which is best seen in FIGS. 22, 23, and 26. The details of this outlet port assembly will be described presently.

Overlying base 162 is a deformable member shown here as an elastomeric, generally planar distendable membrane 184. Superimposed over base 162 and membrane 184 in a membrane clamping relationship is a formed cover means, or cover assembly 186 which is also preferably constructed of a heat formable thermo plastic material. It is to be understood that both base 162 and cover assembly 186 can be constructed from a wide variety of materials and can be sealably interconnected with membrane 184 in a number of ways well known in the art including mechanical, adhesive and thermo bonding. Affixed to the cover member is a use and instruction label 45 of the character previously described. When cover means 186 is interconnected with base 162 in the manner shown in FIG. 24, the cover means sealably encapsulates membrane 184. More particularly, as best seen in FIG. 24, the central portions of the cover clamp membrane 184 securely against the flat base portions disposed between upstanding portions 164, 166 and 169.

Referring both to FIGS. 22 and 24, it can be seen that the cover member 186 is provided with a first reservoir defining chamber 190 which is superimposed over portion 164 of base 162, a second reservoir defining chamber 192 which is disposed over second portion 166 of base 162, and a third reservoir defining chamber 194 which is disposed over third portion 169. In the manner presently to be described, the inner walls of these chamber-defining portions provide engagement surfaces for engagement by distendable membrane 18.4 when the membrane is distended from a first position in which it is proximate base 162 to a second distended position in which the membrane moves into proximity with the interior walls of chamber-defining portions 190, 192, and 194 of cover 186. As best seen in FIGS. 22, 23, 24 and 26, outlet port assembly 180 communicates with the interior of reservoirs R-1, R-2 and R-3 via passageway 195 (FIG. 23). Reservoirs R-1, R-2 and R-3 are formed between portions 164, 166 and 169 of base 162 and the interior surface 184a of membrane 184 in the manner shown in FIG. 24. With this construction, reservoir R-1 can be filled through inlet port or septum 177a, reservoir R-2 can be filled through inlet port or septum 177b and reservoir R-3 can be filled through septum 177c. As fluid is introduced into each of the reservoirs, distendable membrane 184 will be distended from the first position wherein it is proximate the base to the second position shown in FIG. 24 wherein it cooperates with the base to define the three reservoirs. It is to be understood that the reservoirs can be filled at any desired time with any desired liquid including parenteral fluids, pharmaceuticals or other types of medicaments or chemical agents.

Reservoirs R-1, R-2, and R-3 communicate with passageway 195 via stub passageways 195a, 195b, and 195c respectively. Each of the stub passageways is provided with check valves 197 which control fluid flow therethrough. Passageways 195a, 195b, and 195c include closure means, shown here as push button type closure mechanisms 100. As best; seen in FIGS. 22 and 27, each of the closure mechanisms comprises a frangible disk 102 which is superimposed over membrane 184 and a molded boss 104 (FIG. 22) which is strategically located on base 162. As indicated in FIG. 27, disk 102 in cooperation with membrane 184 normally blocks fluid flow through the stub passageway with which it is associated (here shown as 195a). Covering disk 102, membrane 184 and boss 104 is an accordion-like, yieldably deformable cover section 106 which can be depressed downwardly by the user's finger in the manner shown in FIG. 28. When section 106 is deformed, frangible cover membrane 107 is ruptured and disk 102 is clamped against membrane 184 and boss 104 causing the disk to be crushed in the manner shown in FIG. 28. When pressure on Section 106 is released as shown in FIG. 29, fluid can freely flow past boss 104 and inflated membrane 184 through the stub passageway and into passageway 195. Each of the closure mechanisms is of identical construction and operation to that just described so that each of the stub passageways 195a, 195b and 195c can be selectively opened to permit fluid flow into passageway 195. Each of the reservoirs can be vented by vent means comprising vent apertures V-1, V-2, and V-3 (FIG. 22) provided in cover 186. Aperture V-1 is covered by breathably label 45 while apertures V-2 and V-3 are covered by vent patches L-1 and L-2 respectively.

By way of example, in using the device of this latest form of the invention, reservoir R-1 can be filled with a first fluid component by means of septal port 177a. As fluid flows into the reservoir, distendable membrane 184 will be distended into the reservoir. Reservoir R-2 can next be filled with a second fluid component via septal port 177b. As the second component flows into R-2, membrane 184 will distend into the distended configuration shown in FIG. 24 thereby filling reservoir R-2 with the second component. Next, reservoir R-3 can be filled with a third.

After the three fluid components, which may be parenteral fluids, beneficial agents or chemical elements of the character defined in U.S. Ser. No. 08/046,438, have been introducted into reservoirs R-1, R-2 and R-3, outlet port assembly 180 can be operated to dispense fluid from the device. As seen in FIG. 6, assembly 180 which includes a check valve 180a that blocks fluid flow outwardly from the device via the dispensing port 180b. Assembly 180 is operated by first removing closure cap 180c and opening check valve 180a using a dispensing connector of a type well known to those skilled in the art. With check valve 180a open, fluid will flow outwardly of the device via port 180b and a cannula connected to the patient due to the urging of distended membrane 184 as it returns to its less distended starting configuration.

In addition to using the device of this latter form of the invention for sequential delivery of the first, second and third components, the device can also be used for simultaneously delivering the first, second and third components when mechanisms 100 are operated simultaneously.

Referring to FIGS. 30 through 33, still another embodiment of the invention is there shown. The apparatus of this form of the invention is similar in many respects to the embodiment just described and like numbers are used to identify like components. However, unlike the embodiment of FIGS. 22 through 29, the apparatus of this later form of the invention does not use a distendable membrane as an energy source to expel fluid from the three reservoirs. Rather, the device of this embodiment includes a novel expandable sponge-like assembly 300 which functions as the stored energy source. Assembly 300 is made up of three sponge-like, cellular members 300a and 300b and 300c.

Figure 30:
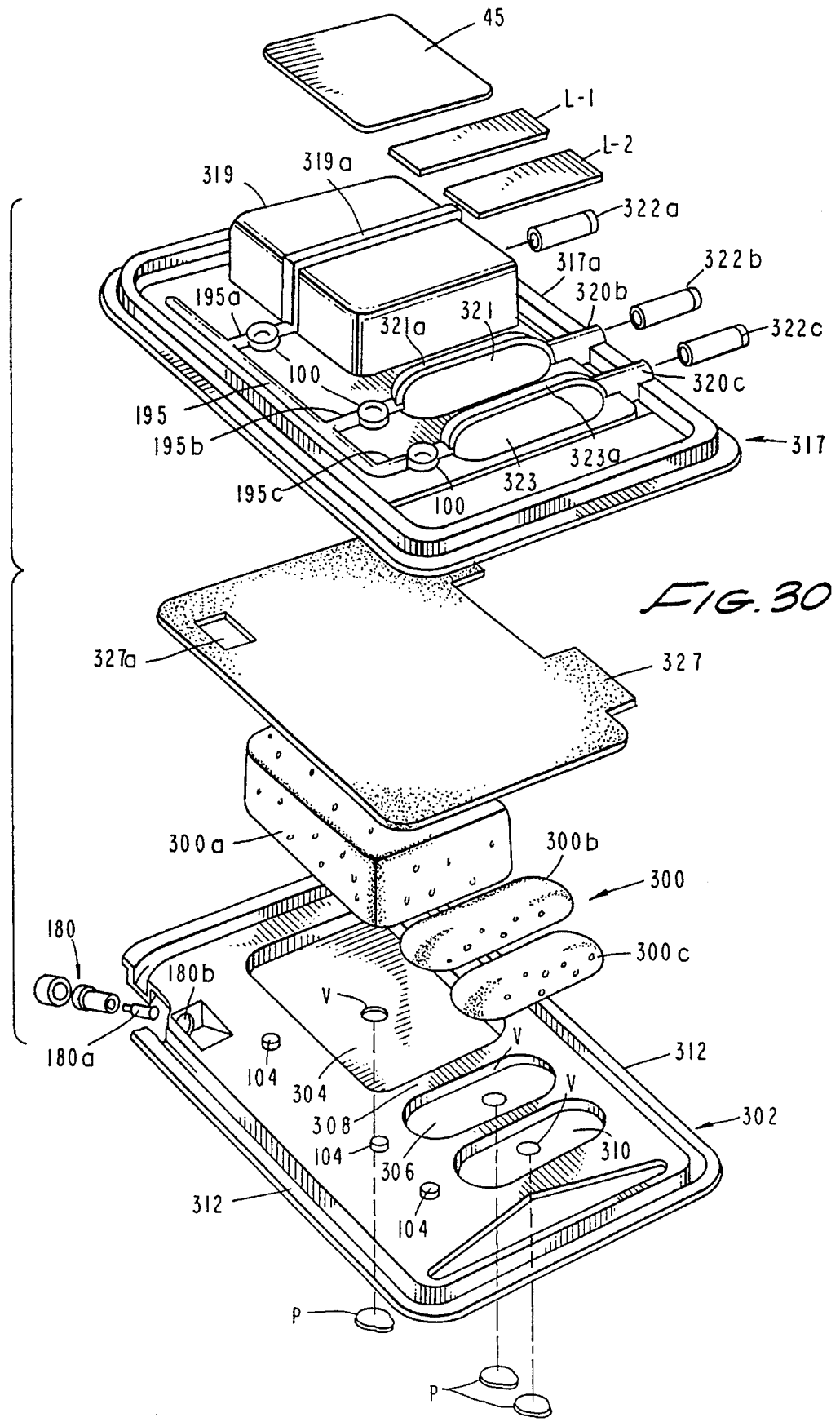
FIG. 30 is a generally perspective, exploded view of yet another embodiment of the fluid dispensing apparatus of the present invention.
Figure 31:
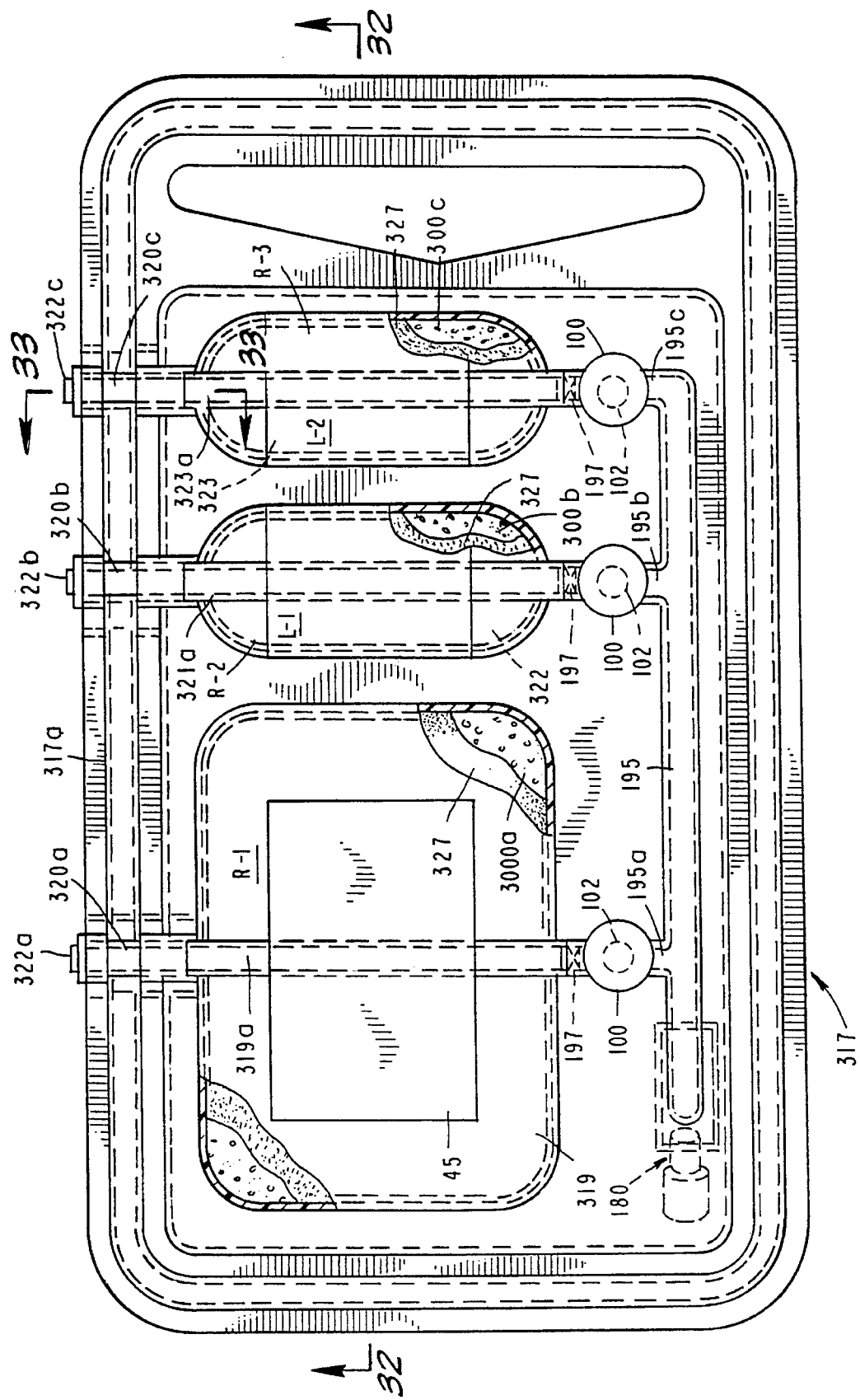
FIG. 31 is a top view of the apparatus shown in FIG. 30 in an assembled configuration.

Turning particularly to FIGS. 30, 31 and 32, the apparatus of this latest form of the invention, comprises a base 302 having a first sump-like recessed portion 304, a second sump-like recessed portion 306, a third portion 308, which is disposed intermediate portions 304 and 306, a fourth sump-like recessed portion 310 and a fifth marginal portion 312 which circumscribes the first, second, third and fourth portions. As before, base 302 is preferably constructed of a thin moldable thermo plastic material which can be thermo formed into the cross-sectional configuration shown in FIG. 32. First, second and fourth portions 304, 306 and 310 receive sponge members 300a, 300b and 300c respectively and are provided with vent means or vent apertures "V" which are initially covered with breathable sealing patches "P".

As best seen in FIG. 31, provided in side wall 317a of cover assembly 317 are fluid inlets comprising channels 320a, 320b and 320c which are adapted to sealably receive fill port means for filling the reservoirs of the device in a manner presently to be described. The fill port means are here shown as septum assemblies 322a, 322b and 322c of standard construction (see also FIG. 31). In a manner presently to be described, the fluid inlets communicate with reservoirs R-1, R-2 and R-3.

Overlying sponge members 300a, 300b and 300c is a deformable barrier member shown here as barrier membrane 327. Superimposed over barrier membrane 327 and base 302 in a membrane clamping relationship is the previously identified cover means, or cover assembly 317 which is preferably constructed of a heat formable thermo plastic material. When cover means 317 is interconnected with base 302 in the manner shown in FIG. 32, the cover means sealably encapsulates barrier membrane 327 as well as the stored energy source, or members 300a, 300b, and 300c. More particularly, as indicated in FIG. 32, the central portions of the cover clamp membrane 327 securely against the flat base portions disposed between the sponge receiving recesses.

Referring both to FIGS. 30 and 32, it can be seen that the cover member 317 is provided with a first reservoir defining chamber 319 which is superimposed over portion 304 of base 302, a second reservoir defining chamber 321 which is disposed over second portion 306 of base 302, and a third reservoir defining chamber 323 which is disposed over fourth portion 310. In the manner presently to be described, the inner walls of these chamber-defining portions provide engagement surfaces for engagement by barrier membrane 327 when the membrane is expanded from a first generally planar position shown by the phantom lines in FIG. 32 to a second expanded position in which the membrane resides proximate the interior walls of chamber-defining portions 319, 321, and 323 of cover 317. As best seen in FIGS. 30 and 31, an outlet port assembly 180, of the character previously described, communicates with the interior of reservoirs R-1, R-2 and R-3 via passageway 195 and aperture 327a provided in membrane 327. With this construction, reservoir R-1 can be filled through inlet port or septum 322a via passageway 319a. Reservoir R-2 can be filled through inlet port or septum 322b via passageway 321a and reservoir R-3 can be filled through septum 322c and passageway 323a (see FIG. 33A). As fluid "F" is introduced into each of the reservoirs, barrier membrane 327 will compress the sponge members 300a, 300b and 300c from a first extended position shown in FIG. 32 to a second more compressed position shown in FIG. 33A. It is to be understood that the reservoirs can be filled at any desired time with any desired liquid including parenteral fluids, pharmaceuticals or other types of medicaments or chemical agents.

As before, reservoirs R-1, R-2, and R-3 communicate with passageway 195 via stub passageways 195a, 195b, and 195c respectively. Each of the stub passageways are provided with rate control means 197 which control the rate fluid flow therethrough. Passageways 195a, 195b, and 195c are provided with closure means, shown here as push button type closure mechanisms 100 of the character previously described. Each of the closure mechanisms comprises a frangible disk 102 and each is operated in the same manner as described in connection with the embodiment of the invention shown in FIGS. 22 through 29.

As was the case with the earlier described embodiment, the device of this latter form of the invention can be used for sequential or simultaneous delivery of first, second and third components.

Turning to FIGS. 34 through 38, yet another embodiment of the invention is there shown. The apparatus of this form of the invention is a three-reservoir construction similar in some respects to the embodiment described in FIGS. 22 through 29. However, the apparatus of this later form of the invention uniquely includes means for interconnecting medicament vials with the three reservoirs and for adding to the fluid contained within the vials selected additives of the character described in Ser. No. 08/046,438.

Figure 34:
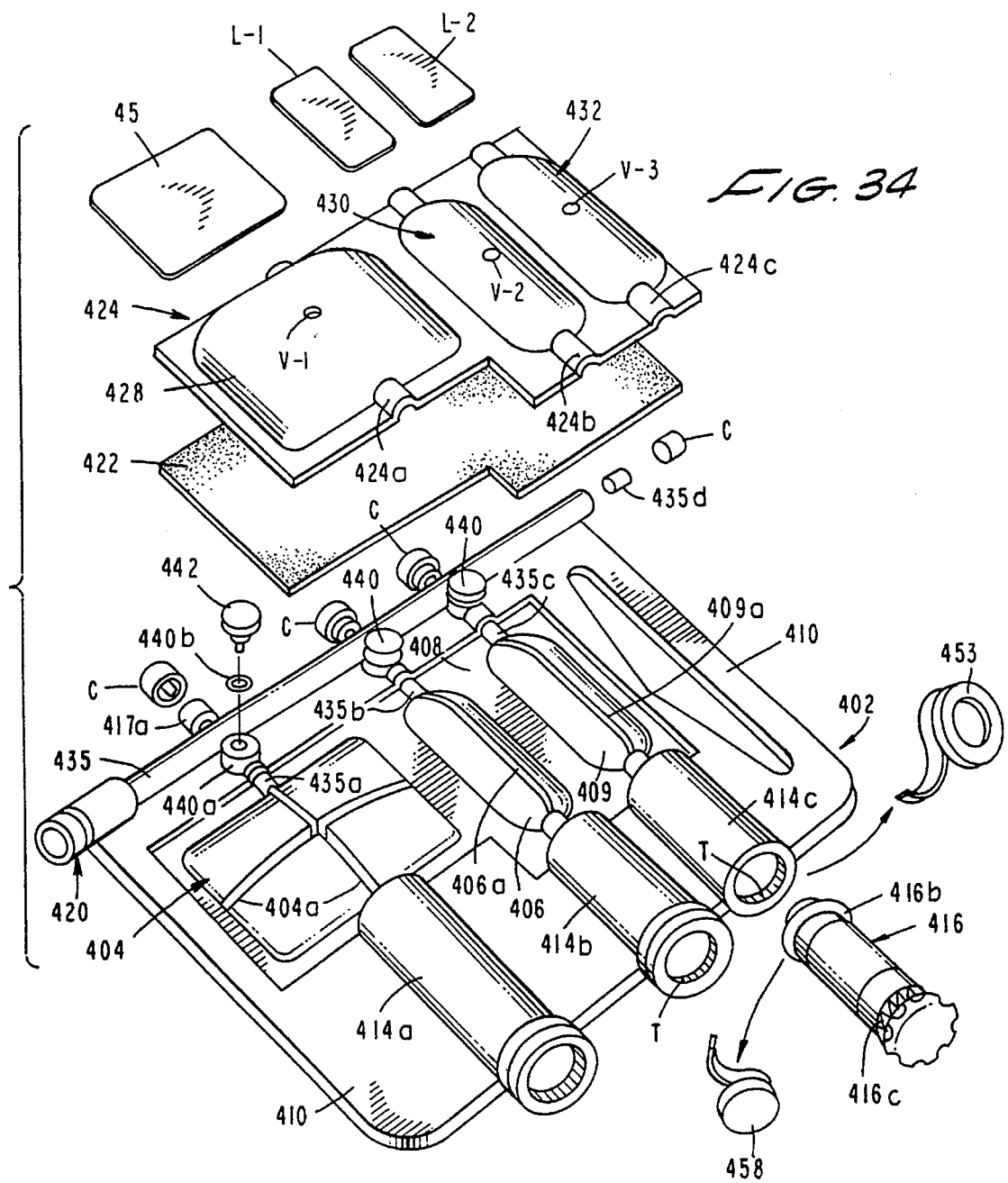
FIG. 34 is a generally perspective exploded view of another embodiment of the apparatus of the present invention.
Figure 36:
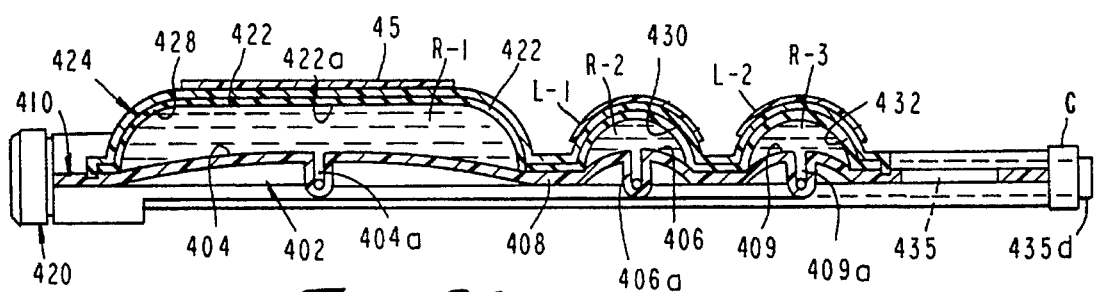
FIG. 36 is a cross-sectional view taken along lines 36—36 of FIG. 35.

Turning particularly to FIGS. 34, 35 and 36, the apparatus of this latest form of the invention, can be seen to comprise a base 402 having a first portion 404, a second portion 406, a third portion 408, which is disposed intermediate portions 404 and 406, a fourth portion 409 and a fifth marginal portion 410 which circumscribes the first, second, third and fourth portions. As before, base 402 is preferably constructed of a thin moldable thermo plastic material which can be injection molded into the cross-sectional configuration shown in FIG. 36. More particularly, first, second and fourth portions 404, 406 and 409 of the base are molded so as to have upstanding central portions which are provided with fluid passageways or fluid channels 404a, 406a and 409a respectively. Provided on base 402 are connector means for interconnection of container means for containing a liquid component. The connector means are here shown as comprising chambers 414a, 414b and 414c which are adapted to mateably receive container means, such as medicament vials 16, for containing a first liquid component.

Vials 416 are adapted to be mated with chambers 414a, 414b, and 414c to accomplish filling the reservoirs of the device in a manner presently to be described. The reservoirs can also be filled via fill port means, here shown as septum assemblies 417a, 417b and 417c which are of the standard construction previously described herein.

Base 402 is provided with a dispensing means or outlet port assembly 420, the configuration of which is best seen in FIG. 35. The details of this outlet port assembly will be described presently.

Overlying a portion of base 402 is a deformable member shown here as an elastomeric, generally planar distendable membrane 422 which is of the character previously described herein and in Ser. No. 08/046,438. Superimposed over a portion of base 402 and membrane 422 in a membrane clamping relationship is a formed cover means, or cover assembly 424 which is preferably constructed of a heat formable thermo plastic material. Affixed to the cover member are breathable patches 45, L-1 and L-2 of the character and function previously described. When cover means 424 is sealably interconnected with base 402 in the manner shown in FIGS. 35 and 36, the cover means sealably encapsulates membrane 422 which, in turn, is sealably connected at the stratigic areas to base 402 (FIGS. 35 and 36). Upraised portions 424a, 424b, and 424c (FIG. 34) are closely received over the neck portions of chambers 414a, 414b, and 414c in the manner indicated in FIG. 37.

Referring to particularly FIG. 34, it can be seen that cover member 424 is provided with a first wall defining a first chamber 428 which is superimposed over portion 404 of base 402. Cover member 424 also includes a second wall defining a second chamber 430 which is disposed over second portion 406 of base 402. Third walls define a third chamber 432 which is disposed over portion 409. As before, the inner walls of these chamber-defining portions provide engagement surfaces for engagement by distendable membrane 422 when the membrane is distended from a first position wherein it is proximate base 402 to a second distended position wherein it moves into proximity with the walls defining chambers 428, 430, and 432 of cover 424. As best seen in FIGS. 34 and 35, outlet port assembly 420 communicates with the interior of reservoirs R-1, R-2 and R-3 via passageway 435 (FIG. 35). Reservoirs R-1, R-2 and R-3 are formed between portions 404, 406 and 409 of base 402 and the interior surface 422a of membrane 422 in the manner shown in FIG. 36.

With the construction described, reservoir R-1 can be filled via the fluid introducing means of the invention which includes connector means or chamber 414a or it can be filled via septum 417a. Similarly, reservoir R-2 can be filled via the connector means or chamber 414b or alternatively it can be filled via septum 417b. In like manner, reservoir R-3 can be filled via septum 417c or filled via chamber 414c. In certain applications, one or more of the reservoirs can also be filled via septum 435d which is provided at one end of passageway 435 (FIG. 35). As fluid is introduced via the fluid introducing means between membrane 422 and each of the first, second and third portions of the base, distendable membrane 422 will be distended from the first position wherein it is proximate the base to the second position shown in FIGS. 36 and 37 wherein it cooperates with the base to define the three reservoirs of this form of the invention. As indicated in FIG. 34, the various septal ports are normally covered by removable caps "C".

Reservoirs R-1, R-2, and R-3 communicate with passageway 435 via stub passageways 435a, 435b, and 435c respectively. Each of the stub passageways is provided with flow rate control means which control fluid flow therethrough. The flow rate control means are here shown as control mechanisms 440, each of which comprises an internally threaded, upstanding cylindrical body portion 440a. As best seen in FIG. 38, body portion 440a is integrally formed with base 402 and is adapted to threadably receive a control knob 442 having a terminal portion 442a which is substantially sealably receivably within passageway 435. By threading knob 442 inwardly and outwardly of threads "T", portion 442a can be moved inwardly and outwardly of flow passageway 435 and in this way can block or precisely control the rate of flow of fluid flowing through the passageway. An elastomeric O ring 440b is provided in portion 440a to prevent leakage past the neck of knob 442.

As before, each of the reservoirs can be vented by vent means comprising vent apertures V-1, V-2, and V-3 (FIG. 34) provided in cover 424. Aperture V-1 is covered by label 45 while apertures V-2 and V-3 are covered by breathable patches L-1 and L-2 respectively.

Referring particularly to FIGS. 34 and 35, chambers 414b and 414c which form a part of the connector means of the invention, each have an additive-containing chamber 450 for containing an additive presentation means such as a scaffold or substrate generally designated in FIG. 35 by the numeral 452. The additive presentation means or substrate 452 can be any type of substrate of the character shown in FIG. 45 of copending U.S. Ser. No. 08/046,438.

Each chamber 414a, 414b and 414c functions as a part of the connector means of the invention and each has a fluid flow path therethrough. Additive presentation means are provided within the fluid flow path of chambers 414b and 414c in the manner shown in FIG. 35. Each of the chambers also has first and second ends, one of which communicates with one of the reservoirs and the other of which is initially sealed by a removable, tear-type sterility plastic cap or cover 453 (FIG. 34). The chambers can be integrally molded with base 402 or they can comprise a glass vial connected to the base or, alternatively they can comprise any other suitable sterile container for housing the additive presentation means and for providing means for the interconnection therewith of the container means such as elution vials 416.

Containers, or elution vials 416, may be of the general character described in copending applicaton Ser. No. 07/986,375 and illustrated therein in FIGS. 1, 3, 4, 5 and 8 (numeral 16). application Ser. No. 07/986,375 is incorporated herein by reference. Containers 416 are preferably sterile containers that include a fluid reservoir 416a (FIG. 35) for containing the liquid component or parenteral fluid of the character defined in copending Ser. Nos. 08/046,438 and 07/983,375.

During the mixing step, containers 416 are telescopically receivable with one of chambers 414b or 414c in the manner shown in FIG. 35. In the present form of the invention, each chamber 416a is closed by a penetrable piston 456 which is telescopically movable within chamber 416a from a first forward position to a rearward position proximate the closed end of container 416. Piston 456 is provided with a plurality of circumferentially extending sealing beads 456a which sealably engage the inner walls 416a of container 416 as the piston moves rearwardly.

A tear-away-type removable sterility cap 458 initially closes the open end of the fluid container. After a selected container 416 has been filled with a suitable first component such as a parenteral fluid "F", piston 456 is inserted into the open end of the container and sterility cap 458 is emplaced over the assemblage thus formed so as to maintain the first component in a sterile, sealed condition until time of use.

Provided proximate the outboard end of each chamber 450 of the connector means 414*b* and 414*c* is a hollow needle assembly 460 which includes a hollow meedle 462. Hollow needle assembly 460, which communicates with the fluid flow path through the connector means, also includes a housing 460*a* which supports hollow needle 462. Needle assembly 460 also includes a check valve 460 which prevents retrograde flow through the flow passageway leading to the reservoir (FIG. 37). Housing 460*a* is positioned within chamber 450 so that hollow needle 462 extends outwardly toward the outboard end of the chamber. With this construction, fluid flowing inwardly through hollow needle 462 will flow past check valve 460 and through passageway 465, which forms a part of the fluid flow path. The fluid then flows around, about and through the additive 467 which is presented to the fluid flow by the additive presentation means 452 in the manner indicated by the arrows in FIG. 35.

In using the apparatus of the invention, caps 453 and 458 are first removed as indicated in FIG. 34. Container 416 is then inserted into the open end of a selected connector means or container receiving chamber 414*b* or 414*c*. As the container is pushed inwardly, needle 462 will penetrate penetrable plug 456 of the container assembly in the manner shown in FIG. 35. Continued inward travel of the container into the connector means causes piston 456 to move inwardly of the container forcing the fluid "F" contained therein to flow outwardly through hollow needle 462 past the check valve and into the fluid flow path within which the additive 467 is strategically positioned. Upon the container seating within the chamber, rotation of the chamber will cause threads 416*b* provided thereon to move into mateable engagement with threads 415 provided proximate the closed or inner end of the container receiving chamber. Locking tabs 416*a* provided on the container will then interlock with teeth "T" provided proximate the open end of chambers 414*b* and 414*c* (FIG. 34) thereby preventing removal of the container. After the fluid "F" has mixed with the additive, the mixture thus formed will flow into the cooperating reservoir, as for example reservoir R-3, causing the distendable membrane to distend outwardly.

Reservoir R-1 can also be filled using a diluent vial of the character identified by the numeral 416 which is mated with the connector means or container receiving chamber 414*a*. Chamber 414*a* has a slightly different construction than that of chambers 414*b* and 414*c* in that it does not contain an internally disposed additive presentation means receiving chamber. Rather, needle 462*a* of this particular connector means communicates directly with a passageway "P" via check valve 460*b*. Passageway P, in turn, communicates directly with reservoir R-1 in the manner shown in FIG. 37.

By mating container 416 with chamber 414*a* in the manner previously described, reservoir R-1 can be filled with a suitable diluent, parenteral or enteral fluid or it can be filled with any other liquid component of the character described in U.S. Ser. No. 08/046,438. As fluid flows between membrane 422 and base portion 404, distendable membrane 422 will be distended in the manner shown in FIG. 36 to form reservoir R-1.

After the various reservoirs are filled, the fluid can be delivered to the patient via a delivery cannula which is threaded into delivery port 420. The delivery cannula DC (FIG. 35) includes a delivery spike "S" of a character well known to those skilled in the art.

With reservoirs R-1, R-2, and R-3 filled in the manner described, the fluid contained therein can be delivered to the patient in any desired sequence by sequentially opening flow control mechanisms 440. Alternatively, part of the fluid contained within reservoir R-3 can be delivered to the patient and then all or a portion of a diluent contained in reservoir R-1 can be immediately administered to the patient. By way of example this delivery can then be followed by delivery of all or part of the fluid contained within reservoir R-2.

In another mode of operation, the delivery cannula DC can be primed using diluent from reservoir R-1. Then medicament from reservoir R-2 can be infused via cannula DC. Following this delivery sequence, cannula DC can be flushed with diluent from R-1 and finally medicament from R-3 can be infused. Subsequently, diluent from R-1 can once again be used to flush cannula DC and the patient can be maintained on KVO (keep vein open) via low rate delivery of diluent from R-1.

It is clear that with the unique design of the apparatus of this latest form of the invention, a wide variety of delivery protocols can be devised to deliver numerous types of beneficial agents in various sequences over various time intervals.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery device for delivering fluids to a patient at a controlled rate comprising:

(a) a base substantially plate like having a width and first and second portions, said first portion having a fluid inlet;

(b) a distendable member overlying and connected to said base;

(c) cover means receivable over said base for sealably enclosing said distendable member, said cover member having a first interior wall portion defining in cooperation with said base a first chamber superimposed over said first portion of said base, and a second interior wall portion defining a second chamber superimposed over said second portion of said base; said cover means further having a fluid inlet passageway in communication with said second portion of said base;

(d) fluid flow means for interconnecting said first and second portions of said base; and (e) said distendable member being movable from a first position proximate said base to a second distended position wherein said member is located proximate said interior wall portions of said cover means upon introduction of fluid under pressure into said fluid inlet of said base, said distendable member in its distended position having a tendency to return toward a less distended position and forming in cooperation with said base a chamber having a height substantially less than said width of said base.

2. A device as defined in claim 1 in which said distendable member comprises an elastomeric membrane.

3. A fluid delivery device for delivering fluids to a patient at a controlled rate comprising:

(a) base having first and second portions, said first portion having a fluid inlet;

(b) a distendable member overlying said base;

(c) cover means receivable over said base for sealably enclosing said distendable member, said cover member having a first interior wall portion defining a first chamber superimposed over said first portion of said base, and a second interior wall portion defining a second chamber superimposed over said second portion of said base; said cover means further having a fluid inlet passageway in communication with said second portion of said base;

(d) fluid flow means for interconnecting said first and second portions of said base; and (e) said distendable member being movable from a first position proximate said base to a second distended position wherein said member is located proximate said interior wall portions of said cover means upon introduction of fluid under pressure into said fluid inlet of said base, said distendable member in its distended position having a tendency to return toward a less distended position, each of said first and second portions of said base include upstanding protuberances engagable by said distendable member when said member is in said first position.

4. A device as defined in claim 3 including closure means for controlling fluid flow through said fluid flow means for interconnecting said first and second portions of said base.

5. A device as defined in claim 4 in which said closure means comprises a wall section of said cover means, said wall section being movable between a first fluid flow means closing position and a second fluid flow means opening position.

6. A fluid delivery device for delivering fluids to a patient at a controlled rate comprising:

(a) a base substantially plate-like having a width and first and second portions, said first portion having a fluid inlet;

(b) a distendable member overlying and connected to said base;

(c) cover means receivable over said base for sealably enclosing said distendable member, said cover member having a first interior wall portion overlying said base and defining in cooperation therewith a first chamber superimposed over said first portion of said base, and a second interior wall portion overlying said base and defining in cooperation therewith a second chamber superimposed over said second portion of said base; said cover means further having a fluid inlet passageway in communication with said second portion of said base;

(d) fluid flow means for interconnecting said first and second portions of said base; and (e) said distendable member being movable from a first position proximate said base to a second distended position upon introduction of fluid under pressure into said fluid inlet of said base, said distendable member in its distended position having a tendency to return toward a less distended position and forming in cooperation with said base first and second fluid chambers each having a height substantially less than said width of said base.

7. A device as defined in claim 6 in which each of said first and second portions of said base include upstanding protuberances engagable by said distendable member when said member is in said first position.

8. A device as defined in claim 6 including closure means for controlling fluid flow through said fluid flow means for interconnecting said first and second portions of said base.

* * * * *